(12) United States Patent
Eichhorn et al.

(10) Patent No.: US 7,738,688 B2
(45) Date of Patent: Jun. 15, 2010

(54) SYSTEM AND METHOD FOR VIEWING VIRTUAL SLIDES

(75) Inventors: Ole Eichhorn, Westlake Village, CA (US); Anne Brumme, Carlsbad, CA (US)

(73) Assignee: Aperio Technologies, Inc., Vista, CA (US)

(*) Notice: Subject to any disclaimer, the term of this patent is extended or adjusted under 35 U.S.C. 154(b) by 0 days.

(21) Appl. No.: 10/787,773

(22) Filed: Feb. 26, 2004

(65) Prior Publication Data

US 2004/0167806 A1 Aug. 26, 2004

Related U.S. Application Data

(63) Continuation-in-part of application No. 09/563,437, filed on May 3, 2000, now Pat. No. 6,711,283, and a continuation-in-part of application No. 10/371,586, filed on Feb. 21, 2003, now Pat. No. 7,035,478.

(60) Provisional application No. 60/451,079, filed on Feb. 28, 2003, provisional application No. 60/485,873, filed on Jul. 9, 2003.

(51) Int. Cl.
*G06K 9/00* (2006.01)
(52) U.S. Cl. ..................... 382/133; 382/128
(58) Field of Classification Search ......... 382/128–134, 382/240
See application file for complete search history.

(56) References Cited

U.S. PATENT DOCUMENTS

| | | | |
|---|---|---|---|
| 3,643,015 A | 2/1972 | Davidovits et al. | |
| 4,673,988 A | 6/1987 | Jansson et al. | |
| 4,700,298 A | 10/1987 | Palcic et al. | |
| 4,742,558 A * | 5/1988 | Ishibashi et al. | 382/240 |
| 4,744,642 A | 5/1988 | Yoshinaga et al. | |
| 4,760,385 A | 7/1988 | Jansson et al. | |
| 4,777,525 A | 10/1988 | Preston et al. | |
| 4,845,552 A | 7/1989 | Jaggi et al. | |
| 4,960,999 A | 10/1990 | McKean et al. | |

(Continued)

FOREIGN PATENT DOCUMENTS

EP 0 339 582 4/1989

(Continued)

OTHER PUBLICATIONS

Catalyurek et al, "The Virtual Microscope", IEEE Transactions on Information Technology in Biomedicine, vol. 7, No. 4, Dec. 2003.*

(Continued)

*Primary Examiner*—Tom Y Lu
(74) *Attorney, Agent, or Firm*—Pattric J. Rawlins; Procopio Cory Hargreaves & Savitch LLP

(57) ABSTRACT

Virtual slide image data and corresponding information are stored in a data storage area on a virtual slide image server. A client viewer requests image data at a particular resolution. The image server obtains corresponding image data from the data storage area at a resolution nearest to the requested resolution. The image data is then sent to the client viewer. The client viewer receives the image data and scales the image data to the requested resolution prior to displaying the image data.

16 Claims, 30 Drawing Sheets

U.S. PATENT DOCUMENTS

| | | | |
|---|---|---|---|
| 5,086,477 A | | 2/1992 | Yu et al. |
| 5,187,754 A | | 2/1993 | Currin et al. |
| 5,231,663 A | | 7/1993 | Earl et al. |
| 5,257,182 A | * | 10/1993 | Luck et al. ............... 382/224 |
| 5,400,145 A | | 3/1995 | Suita et al. |
| 5,412,214 A | | 5/1995 | Suzuki et al. |
| 5,495,535 A | | 2/1996 | Smilansky et al. |
| 5,578,832 A | | 11/1996 | Trulson et al. |
| 5,633,948 A | | 5/1997 | Kegelmeyer, Jr. |
| 5,644,356 A | | 7/1997 | Swinson et al. |
| 5,672,861 A | | 9/1997 | Fairley et al. |
| 5,710,835 A | * | 1/1998 | Bradley ............... 382/233 |
| 5,714,756 A | | 2/1998 | Park et al. |
| 5,734,915 A | * | 3/1998 | Roewer ............... 715/202 |
| 5,790,710 A | | 8/1998 | Price et al. |
| 5,793,969 A | * | 8/1998 | Kamentsky et al. ......... 709/213 |
| 5,796,861 A | | 8/1998 | Vogt |
| 5,834,758 A | | 11/1998 | Trulson et al. |
| 5,872,591 A | | 2/1999 | Truc et al. |
| 5,912,699 A | | 6/1999 | Hayenga et al. |
| 5,922,282 A | | 7/1999 | Ledley |
| 5,943,122 A | | 8/1999 | Holmes |
| 5,963,314 A | | 10/1999 | Worster et al. |
| 5,968,731 A | * | 10/1999 | Layne et al. ............... 435/5 |
| 5,991,444 A | | 11/1999 | Burt et al. |
| 5,999,662 A | | 12/1999 | Burt et al. |
| 6,002,789 A | | 12/1999 | Olsztyn et al. |
| 6,005,964 A | | 12/1999 | Reid et al. |
| 6,049,421 A | | 4/2000 | Raz et al. |
| 6,078,681 A | * | 6/2000 | Silver ............... 382/133 |
| 6,091,846 A | | 7/2000 | Lin et al. |
| 6,101,265 A | | 8/2000 | Bacus et al. |
| 6,137,897 A | * | 10/2000 | Emi et al. ............... 382/128 |
| 6,183,795 B1 | | 2/2001 | Yates |
| 6,272,235 B1 | * | 8/2001 | Bacus et al. ............... 382/133 |
| 6,314,452 B1 | * | 11/2001 | Dekel et al. ............... 709/203 |
| 6,327,377 B1 | | 12/2001 | Rutenberg et al. |
| 6,330,348 B1 | | 12/2001 | Kerschmann et al. |
| 6,438,268 B1 | | 8/2002 | Cockshott et al. |
| 6,519,357 B2 | | 2/2003 | Takeuchi |
| 6,556,724 B1 | * | 4/2003 | Chang et al. ............... 382/299 |
| 6,711,283 B1 | | 3/2004 | Soenksen |
| 6,714,281 B1 | | 3/2004 | Amano et al. |
| 6,829,378 B2 | * | 12/2004 | DiFilippo et al. ........... 382/128 |

FOREIGN PATENT DOCUMENTS

| | | |
|---|---|---|
| EP | 0 871 052 | 10/1998 |
| WO | 98/39728 | 9/1998 |
| WO | 98/44446 | 10/1998 |
| WO | 01/26541 | 4/2001 |

OTHER PUBLICATIONS

Hamilton, Eric, "JPEG File Interchange Format" Version 1.02, Sep. 1, 1992; C-Cube Microsystem, Milpitas, CA.

Adobe Developers Association, "TIFF" Revision 6.0, Jun. 3, 1992; Adobe Systems Incorporated, Mountain View, CA.

International Preliminary Report on Patentability from PCT/US04/06012 dated Jul. 8, 2005.

International Search Report and Written Opinion from PCT/US04/06012 dated Apr. 12, 2005.

Checksum— Wikipedia, the free encyclopedia. Retrieved from internet: http://en.wikipedia.org/wiki/Checksum.

Apr. 22, 2009 English translation of Notice of Reasons for Rejection from JP2006-503911.

Dunn Bruce et al., "Dynamic-robotic telepathology: Department of Veterans Affairs Feasibility Study", "Human Pathology", 1997, vol. 28, Nr 1.pp. 8-12, ISSN 0046-8177.

Hadida-Hassan M. et al., "Web-based telemicroscopy", "Journal of Structural Biology", Apr.-May, 1999, vol. 125, Nr 2-3, pp. 235-245, ISSN 1047-8477.

May 8, 2007 European Communication with Supplementary European Search Report for European Patent Application No. 04715770.6.

Apr. 21, 2009 European Communication for European Patent Application No. 04715770.6.

May 16, 2008 European Communication for European Patent Application No. 04715770.6.

Sep. 19, 2007 European Communication for European Patent Application No. 04715770.6.

Jan. 26, 2007 European Communication with partial European Search Report for European Patent Application No. 04715770.6.

Oct. 6, 2005 European Communication for European Patent Application No. 04715770.6.

* cited by examiner

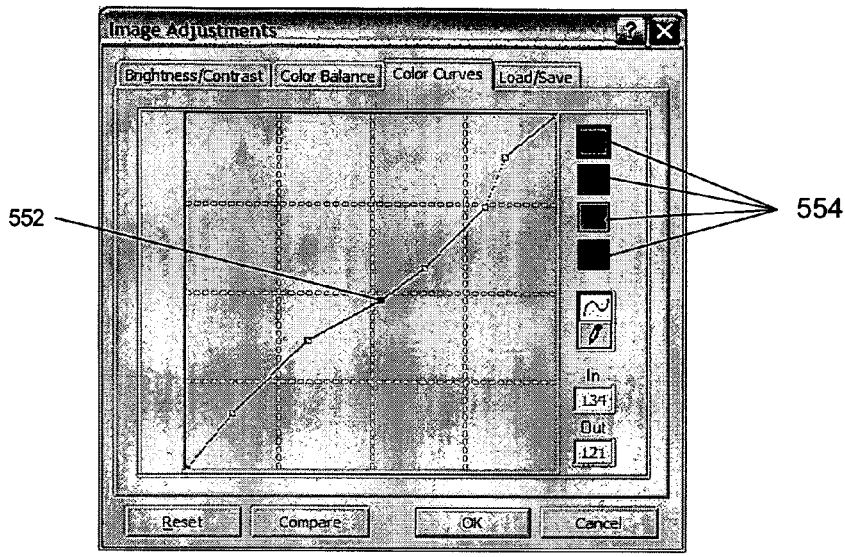
FIG. 5E
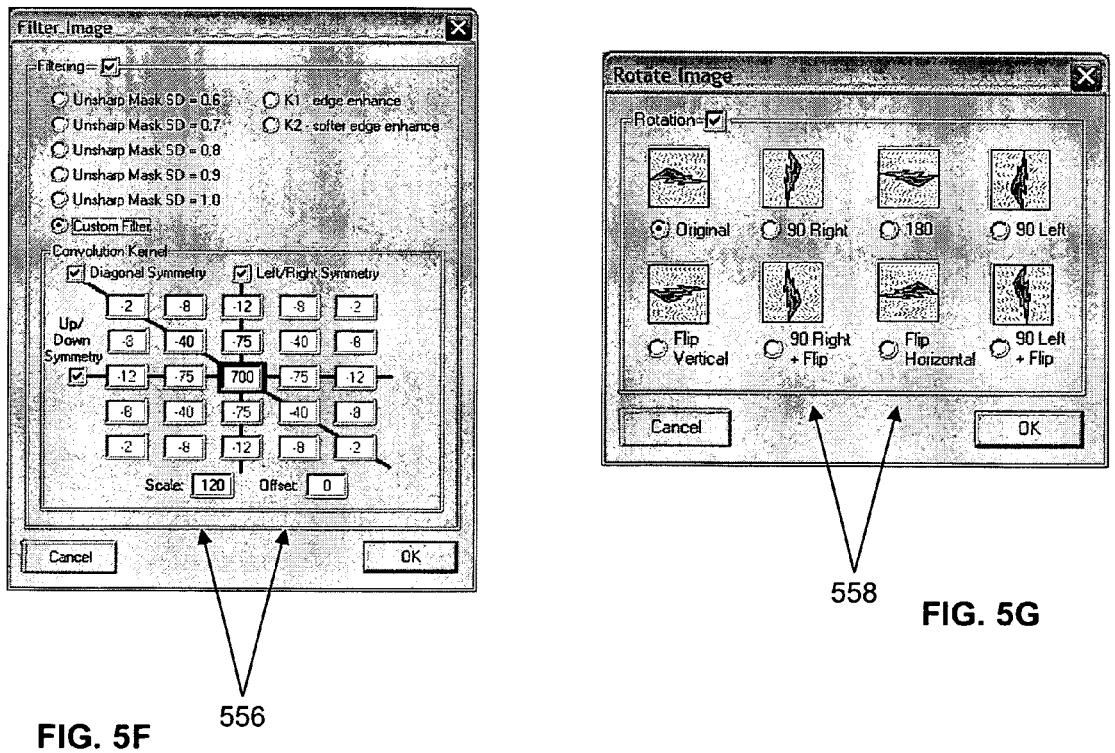
FIG. 5F
FIG. 5G

SYSTEM AND METHOD FOR VIEWING VIRTUAL SLIDES

RELATED APPLICATION

The present application is a continuation-in-part of Ser. No. 09/563,437, now U.S. Pat. No. 6,711,283 filed on May 3, 2000 and a continuation-in-part of Ser. No. 10/371,586, now U.S. Pat. No. 7,035,478 filed on Feb. 21, 2003 and claims priority to U.S. provisional patent application Ser. No. 60/451,079 filed on Feb. 28, 2003 and U.S. provisional patent application Ser. No. 60/485,873 filed on Jul. 9, 2003, each of which is incorporated herein by reference in its entirety.

BACKGROUND

1. Field of the Invention

The present invention generally relates to computer facilitated viewing of large images and more specifically relates to computer facilitated viewing of virtual microscope slides.

2. Related Art

In the growing field virtual microscopy, the first challenges to be overcome were related to the digital imaging of microscope slides ("scanning"). Conventional image tiling is one approach that is widely prevalent in the virtual microscopy industry. The image tiling approach to scanning microscope slides employs a fixed area charge coupled device ("CCD") camera and takes hundreds or thousands of individual pictures ("image tiles") of adjacent areas of the microscope slide. These image tiles are stored in a computer and an index is used to identify the name of each image tile and its relative location in the macro image. A conventional image tiling approach is described in U.S. Pat. No. 6,101,265. Although slow and cumbersome, conventional image tiling solutions did succeed in scanning microscope slides to create a virtual slide.

Once the virtual slide was present in a computer system, the viewing of portions of the slide was relatively straight forward based on the inherent nature of the thousands of image tiles. If a user wanted to view a portion of a virtual slide, all the user had to do was select the portion and then the system could identify the corresponding individual image tiles and display those tiles. Accordingly, the viewing aspect of virtual microscopy was not very challenging for conventional image tiling solutions.

In particular, a new linear array based line scanning solution has been developed by Aperio Technologies, Inc. This solution employs a linear-array detector in conjunction with specialized optics, as described in U.S. Pat. No. 6,711,283 entitled "Fully Automatic Rapid Microscope Slide Scanner," which is currently being marketed under the name ScanScope®.

More recently, significantly improved systems for creating virtual slides have been introduced into the virtual microscopy industry. Aperio Technologies, Inc. now provides a linear array based line scanning solution as described in U.S. Pat. No. 6,711,283. The revolutionary line scanning solution reduces the time to create a virtual slide from hours to minutes. In addition to rapid data capture, line scanning benefits from several advantages that ensure consistently superior imagery data. First, focus of the linear array can be adjusted from one scan line to the next, in contrast to image tiling systems that are inherently limited to a single focal plane for an entire image tile. Second, because the linear array sensor in a line scanning system is one-dimensional, there are no optical aberrations along the scanning axis. In an image tiling system, the optical aberrations are circularly symmetric about the center of the image tile. Third, the linear array sensor has a complete (100%) fill factor, providing full pixel resolution (8 bits per color channel), unlike color CCD cameras that lose spatial resolution because color values from non-adjacent pixels must be interpolated (e.g., using a Bayer Mask).

Another significant improvement provided by the line scanning solution is that a virtual slide is contained in a single image file on the computer system, in stark contrast to the thousands of individual image tiles created by a conventional image tiling system. Managing a single image file for a virtual slide requires significantly less operating system overhead than the management of thousands of individual image tiles and the corresponding index. However, the creation of a single image file for a virtual slide, while much more efficient and less time consuming, creates new challenges for the viewing of these virtual slides. A virtual slide file created by a line scanner can be up to 4 gigabytes ("GB") in size as opposed to the 1 MB size for an image tile.

Therefore, introduction of the superior line scanning system for creating virtual slides has created a need in the industry for virtual slide viewing systems and methods that meet the unique needs imposed by the new technology.

SUMMARY

The present invention provides a virtual slide image file format that facilitates the viewing of large amounts of visual image data on a standalone device or over a local or wide area network. Virtual slide image data and corresponding information are stored in a data storage area on a virtual slide image server that provides high performance access to virtual slide image data and corresponding information. A client viewer configured to efficiently display and manipulate virtual slide image data requests image data at a particular resolution. The image server obtains corresponding image data from the data storage area at a resolution nearest to the requested resolution. The image data is then sent to the client viewer. The virtual slide client viewer receives virtual slide image data at the stored resolution and subsequently scales the image data to the appropriate resolution for viewing. Accordingly, a virtual slide image that was scanned at a baseline resolution can be viewed at any higher resolution without loss of image fidelity. A web based system is also provided.

Additionally, the virtual slide image server facilitates simultaneous collaborative viewing of virtual slides by a leader client viewer and several participating client viewers. The participating client viewers are restricted from manipulating the virtual slide being viewed, although the leader of the collaborative session may turn over the leader role to a participating client viewer, after which the new leader has viewing control and the prior leader is demoted to a participating client.

The present invention also provides for three dimensional viewing of virtual slides. A specimen on a microscope slide is scanned at a plurality of vertical levels and a separate virtual slide image is created for each vertical level. When a view of the composite virtual slide image is requested and the requested level falls between the two scanned levels, the immediate upper level and immediate lower level are interpolated to produce the requested viewing level without a loss of image fidelity. Additionally, three dimensional views can be provided by shifting image pixels in the immediate upper level image in a first direction and shifting image pixels in the immediate lower level image the opposite direction to provide a skewed image of the requested level allow three dimensional viewing of the composite image.

BRIEF DESCRIPTION OF THE DRAWINGS

The details of the present invention, both as to its structure and operation, may be gleaned in part by study of the accompanying drawings, in which like reference numerals refer to like parts, and in which:

FIG. 5D-H are screen shots illustrating example viewing windows and manipulation control windows according to an embodiment of the present invention;

DETAILED DESCRIPTION

Certain embodiments as disclosed herein provide for systems and methods for viewing virtual microscope slides, which are extremely large images having file sizes up to 4 GB (containing up to 100 GB of raw image data prior to compression). The present invention provides fast and efficient systems and methods for accessing such large imagery files and displaying the corresponding imagery data on a local or remote viewing station. For example, one method as disclosed herein allows for a client viewer to request image data from a virtual slide image file at a particular resolution. The server system fetches a compressed block of imagery data that comprises imagery data at a resolution near the requested resolution and sends the data block to the client. The client then scales the imagery data and presents the image at the requested resolution.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
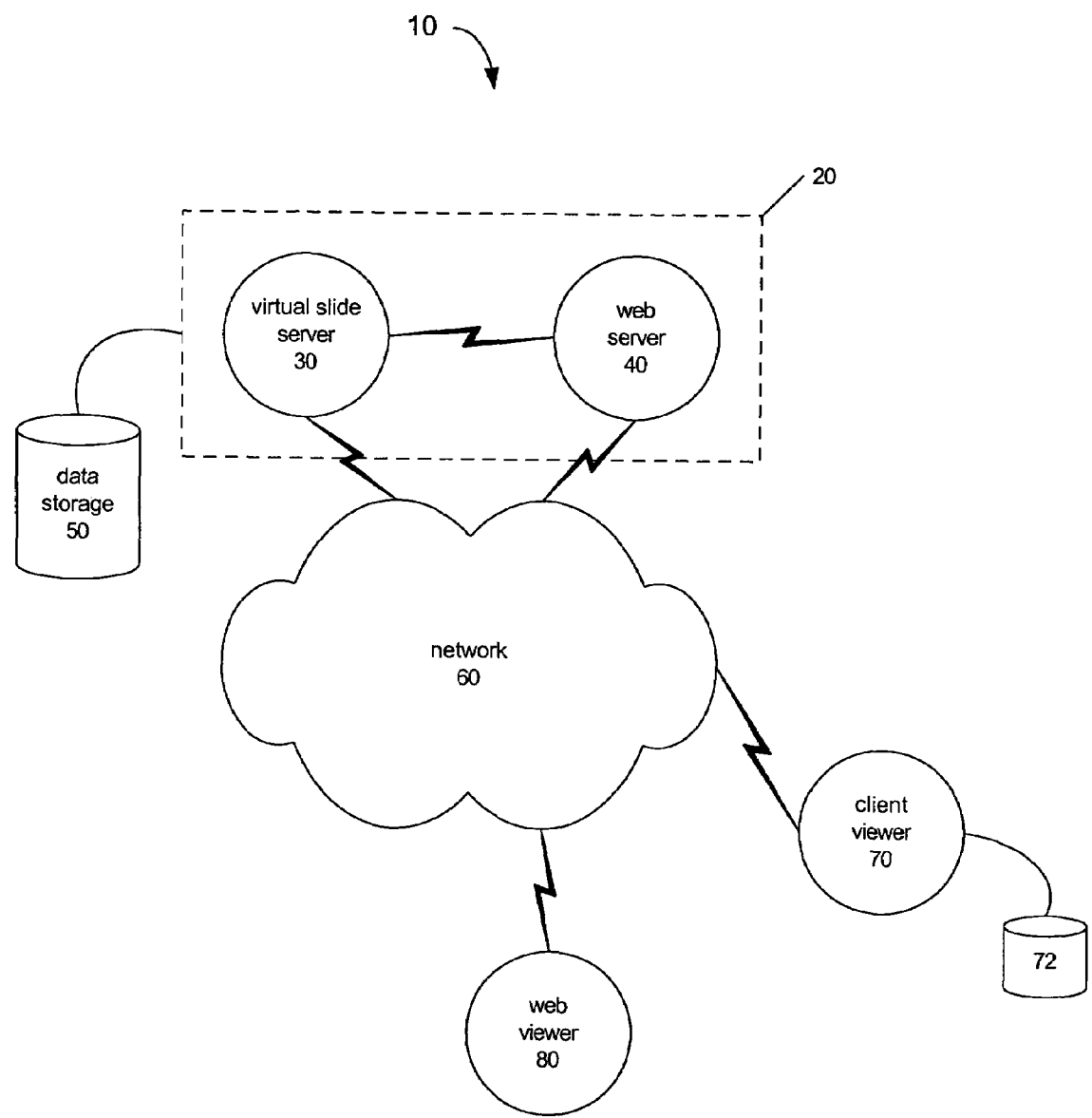
FIG. 1 is a network diagram illustrating an example system for viewing virtual slide images according to an embodiment of the present invention.

FIG. 1 is a network diagram illustrating an example system 10 for viewing virtual slide images according to an embodiment of the present invention. In the illustrated embodiment, the system 10 comprises a virtual slide server 30 communicatively coupled with a client viewer 70 and a web viewer 80 over a network 60. There may be multiple client viewers 70 and multiple web viewers 80. Additionally, a web server 40 may be included with the system 10. The web server 40 may be separate, as shown, or co-located with the virtual slide server into a combined server 20. The combined server 50 is configured with a data storage area 50. Alternatively, if the virtual slide server 30 is separate from the web server 40, then each separate server is preferably configured with its own data storage area (not shown). In such an embodiment, the virtual slide server 30 may have a data storage area to store virtual slide image data (among other data), and the web server 40 may have a data storage area to store web page data (among other data).

Client viewer 70 is also configured with a data storage area 72. The data storage area can preferably be used to locally store virtual slide images and other data and information to facilitate the viewing of virtual slides. Web viewer 80 does not require a data store because caching is preferably performed using computer memory rather than local disk storage. In alternative embodiments, a data storage area may be included.

Network 60 may comprise any of a variety of network topologies and physical layers. For example, network 60 may be a local area network ("LAN"), wide area network ("WAN"), a wireless wide area network ("WWAN") or a combination of networks such as the Internet. Moreover, the network 60 may employ different communication protocols such as TCP/IP, and the like, and application protocols such as HTTP, and the like.

Figure 2A:
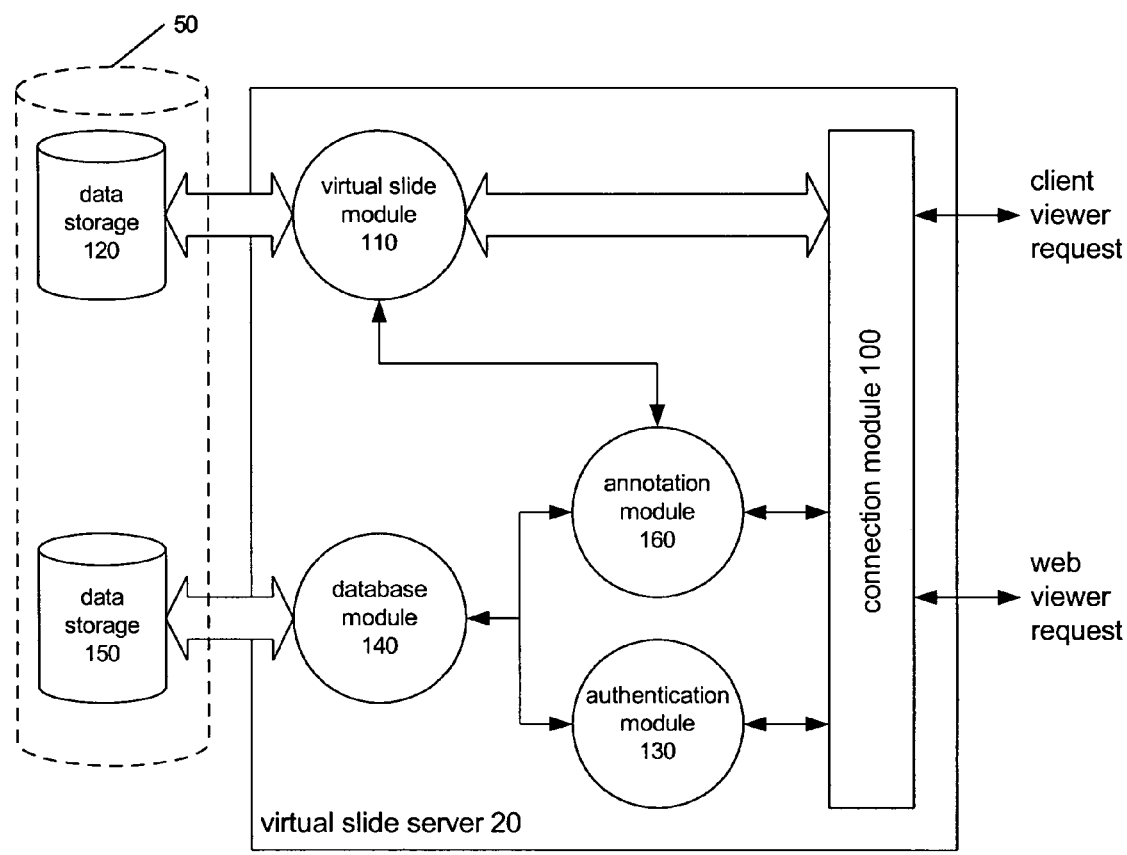
FIG. 2A is a block diagram illustrating an example virtual slide server according to an embodiment of the present invention.

FIG. 2A is a block diagram illustrating an example virtual slide server 20 according to an embodiment of the present invention. In the illustrated embodiment, the virtual slide server 20 comprises a connection module 100, a virtual slide module 110, an annotation module 160, an authentication module 130, and a database module 140. The server 20 is configured with a data storage area 50. Alternatively, data storage area 50 may be physically or logically (or both) separated into two or more separate data storage areas such as data storage area 120 and data storage area 150. Data storage area 120 contains virtual slide image data and data storage area 150 contains annotation and user authentication information, and perhaps other administrative data such as virtual slide case information.

The connection module 100 is preferably configured to receive requests from a client viewer or a web viewer. A request may seek information, image data, or both. Additionally, a request may provide information such as authentication information or annotation information. Although shown separately, the annotation module 160 and authentication module 130 may be part of the connection module 100.

Requests related to virtual slide images are routed by the connection module 100 to the virtual slide module 110. The virtual slide module obtains image data from data storage area 120 and processes the image data when necessary and sends a response back to the requesting viewer (client viewer or web viewer). The virtual slide module may also communicate with the annotation module 160 to provide annotation layovers for the virtual slide images. The annotation module 160 maintains discrete layers of annotations for the various virtual slide images and facilitates the creation and modification of annotations as well as the display of the annotation layers in conjunction with the virtual slide module 110.

The authentication module 130 is configured to validate viewers that are sending in requests. The authentication module 130 may maintain a database of users and passwords or other authentication information (e.g., IP address) so that sensitive virtual slide image data and/or associated database information are not inadvertently provided to an unauthorized requesting viewer. This database may be maintained in the data storage area 150. The various modules that store data in the data storage area 150 may access that data through database module 140. In one embodiment, the modules may store data in a conventional file system in data storage area 150 and therefore not need the overhead of an actual database structure. However, certain advantages and optimizations can be realized through the use of a database in conjunction with the data storage area 150 and in such a case, the database module 140 can facilitate communication with the database, including queries, fetches, stores, and the like.

Figure 2B:
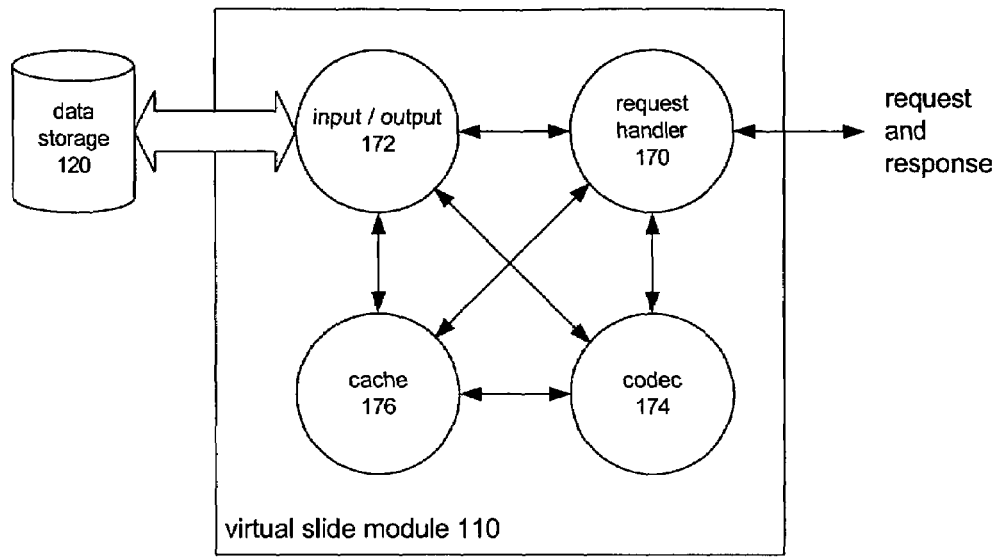
FIG. 2B is a block diagram illustrating an example virtual slide module according to an embodiment of the present invention.

FIG. 2B is a block diagram illustrating an example virtual slide module 110 according to an embodiment of the present invention. In the illustrated embodiment, the virtual slide module 110 comprises a request handler 170, an input/output ("I/O") module 172, one or more data encoder/decoders ("codecs") 174, and an image cache 176. The I/O module 172 accesses the data storage area 120 to retrieve and store virtual slide image data and other related virtual slide information. For example, requests for virtual slide image data are fetched from the data storage area 120 by the I/O module 172. Additionally, an orthogonal rotation or newly scaled level in a virtual slide image may be stored by the I/O module 172 in the image cache 176.

The request handler is configured to identify the type of request received. For example, the request may be for a particular block of a virtual slide image or the request may be for a particular sub-region of the virtual slide image. The request may also be for information about the virtual slide. The difference between a block and a sub-region of a virtual slide image file is grounded in the structure of the virtual slide image file, as explained in detail later with respect to FIGS. 4A-4F. Initially, however, a block is a predefined data block that is inherent in the file structure of the stored virtual slide image. A sub-region, in contrast, is an arbitrary area of the virtual slide image that may be a subset of a single block or any combination of two or more blocks. Accordingly, fetching blocks is extremely efficient while fetching and constructing sub-regions is more processor intensive.

A codec 174 is preferably configured to implement various different compression techniques. In a preferred embodiment JPEG2000 compression is employed for virtual slide image files and therefore codec 174 is configured to compress and decompress according to the JPEG2000 standard. Additionally, a codec 174 may be configured to also compress and decompress according to the JPEG and Lempel-Ziv Welch ("LZW") compression standards, as well as other lossless and lossy image compression techniques. The virtual slide module 110 may support multiple compression technologies concurrently, in which case there will be multiple instances of codec 174, selected based on image attributes.

The cache 176 may be implemented as a single physical cache or as a plurality of separate physical caches. In one embodiment, several logically discrete caches are used by the virtual slide module 110, include a cache for image blocks, a cache for image sub-regions, and a cache for virtual slide information.

Figure 2C:
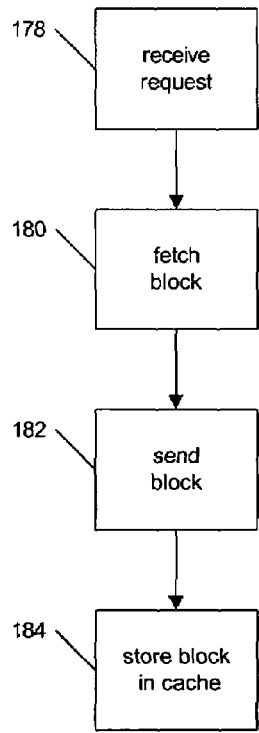
FIG. 2C is a flow diagram illustrating an example process for handling a virtual slide image block request according to an embodiment of the present invention.

FIG. 2C is a flow diagram illustrating an example process for handling a virtual slide image block request according to an embodiment of the present invention. Initially, in step 178, the virtual slide module receives the request from the client viewer. The request is received by the request handler and passed to the I/O module for processing. In step 180, the I/O module fetches the requested block from the data storage area and passes the block back to the request handler. Alternatively, the I/O module can first check a cache to see if the image data is available there. Next, the request handler sends the requested block to the requesting viewer in step 182 and then stores the requested block in the block cache, as illustrated in step 184.

Additionally, the request handler or the I/O module may execute a predictive function to determine the likelihood of an adjacent or other block being requested. If it is determined that the likelihood exceeds a certain threshold, then the identified block may be pre-fetched by the I/O module from data storage and temporarily placed in the block cache in anticipation of the request. Such a pre-fetch function may advantageously significantly improve the operation of the viewing system overall. The pre-fetch predictive function may implement heuristics based on previous requests and user access patterns.

Figure 2D:
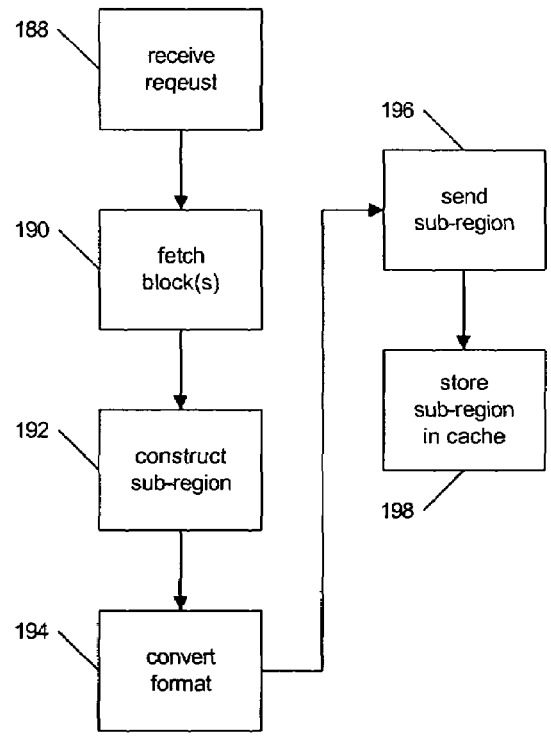
FIG. 2D is a flow diagram illustrating an example process for handling a virtual slide image sub-region request according to an embodiment of the present invention.

FIG. 2D is a flow diagram illustrating an example process for handling a virtual slide image sub-region request according to an embodiment of the present invention. In step 188, the request handler receives the request and then passes the request to the I/O module for data retrieval. The I/O module fetches from the cache or data storage the block or blocks needed to construct the sub-region, as shown in step 190. Once the block or blocks have been obtained, the sub-region is constructed in step 192 and then in step 194 the format of the sub-region is converted.

Converting the format of the sub-region is often necessary when providing image data to a web viewer client if the particular web viewer client is not compatible with the native format, for example JPEG2000. In addition to compression format, additional conversions may be performed to scale image data, transform image data (rotate or flip), perform color correction, apply convolution matrices, etc. These steps may all be performed by the request handler on behalf of requesting clients. Additionally, in an alternative embodiment, the step of constructing a sub-region by converting image data can advantageously be carried out by the client viewer program on the requesting side of the viewing system. Accordingly, the sub-region construction and conversion steps may only be necessary when the request is received from a web viewer client or other viewing client that cannot request and process images at the block level, which is more efficient.

Once the sub-region is constructed and the image converted (if necessary), the resulting sub-region is then sent to the requesting viewer, as illustrated in step 196. Upon sending the sub-region, the virtual slide module preferably stores the sub-region in a sub-region cache, as shown in step 198.

Figure 3:
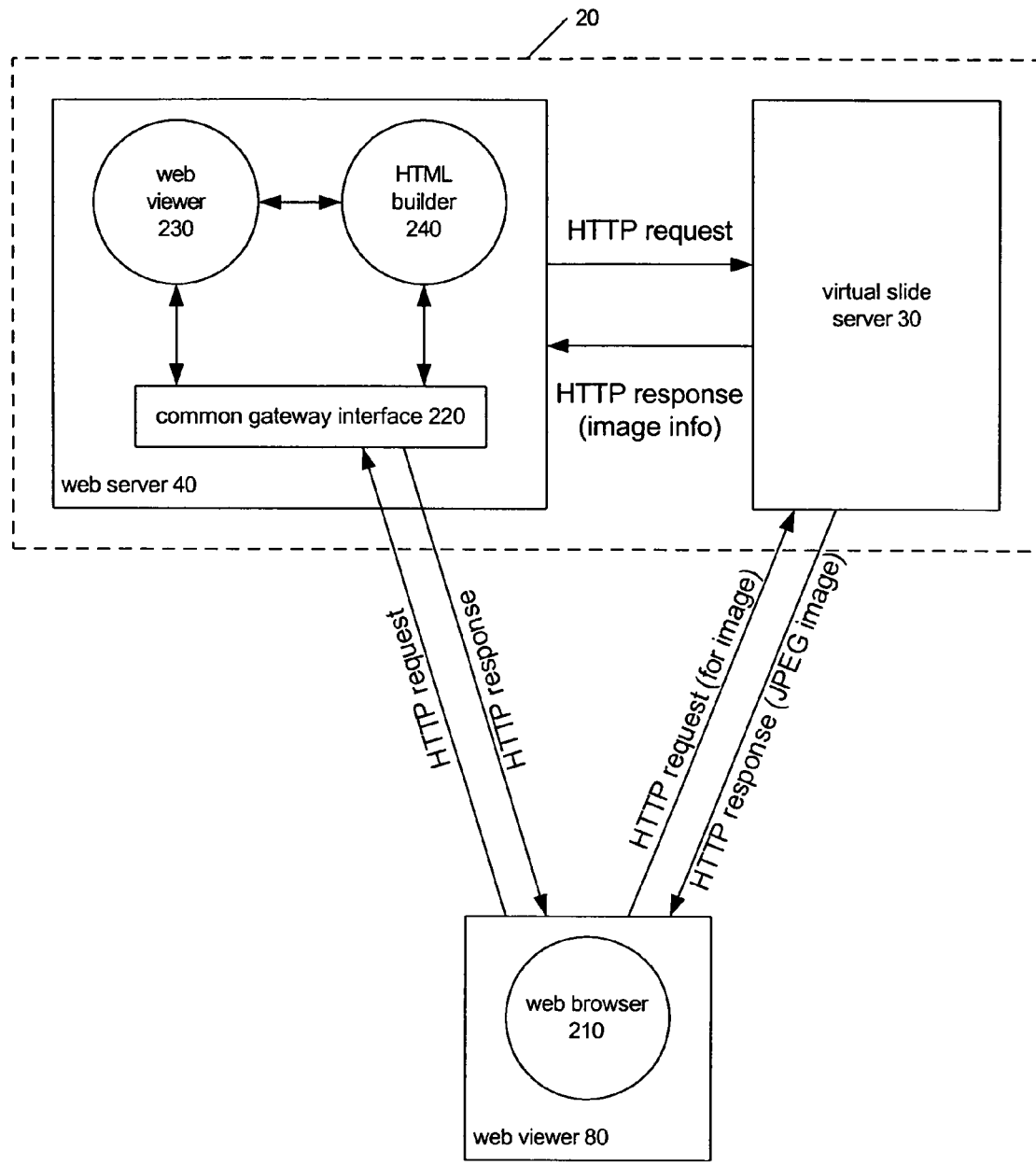
FIG. 3 is a network diagram illustrating an example web server for viewing virtual slide images according to an embodiment of the present invention.

FIG. 3 is a network diagram illustrating an example web server 40 for viewing virtual slide images according to an embodiment of the present invention. In the illustrated embodiment, a web viewer client 80 is communicatively coupled with the web server 40 via a network (not shown). Advantageously, the web viewer client comprises just a standard web browser 210 with no specialized software modules.

The web server 40 comprises a common gateway interface ("CGI") 220, a web viewer 230, and an HTML builder. In one embodiment, the HTML builder may be implemented as part of the web viewer 230. Also shown in the illustrated embodiment is the virtual slide server 30, which maintains and provides the image data and other information related to virtual slides.

As shown, the web viewer 80 sends an HTTP request to the web server 40 requesting a virtual slide. The CGI 220 receives the request and passes it to the web viewer 230 which then sends a corresponding virtual slide request to the virtual slide server 30 via an HTTP request. The virtual slide server 30 responds to the request with an HTTP response comprising image information. The HTTP response to the web server 40 does not include actual image data but includes other information such as image attributes. On the web server 40, after receiving the HTTP response from the virtual slide server 30, the web viewer 230 constructs the HTTP response for the web viewer 80, in conjunction with the HTTP builder 240. Preferably, the HTTP response provides the web browser 210 with the HTML framework for displaying the virtual slide image and includes an image tag reference for the native image data (e.g., JPEG). The web browser 210, during its processing of the HTTP response from the web server 40, encounters the image tag reference and accordingly causes the web viewer 80 to send an HTTP request to the virtual slide server 30 seeking the image data. In response to the request from the web viewer 80, the virtual slide server sends the image data in a format that can be displayed by the web browser 210.

Figure 4A:
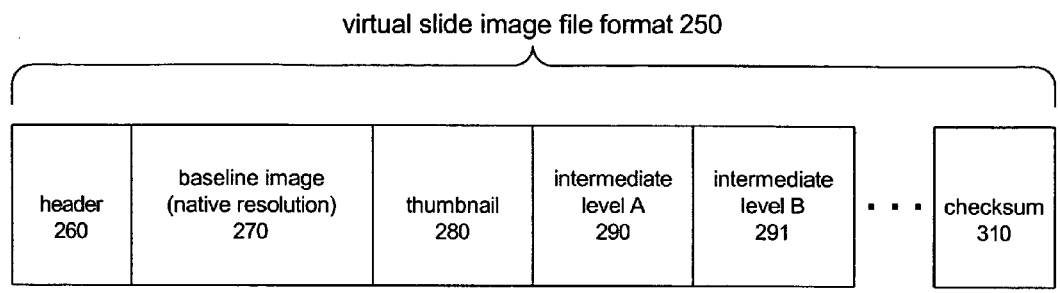
FIG. 4A is a block diagram illustrating an example virtual slide file format according to an embodiment of the present invention.

FIG. 4A is a block diagram illustrating an example virtual slide file format 250 according to an embodiment of the present invention. The virtual slide image file comprises a plurality of images, which are each an image of the entire virtual slide at a different resolution. In one embodiment, when the virtual slide is created, a certain number of intermediate level images are also created and stored in the virtual slide image file in order to provide more efficient zooming access when viewing the virtual slide.

In the illustrated embodiment, the file format comprises a header 260 and a checksum 310. The checksum 310 may be optional. In one embodiment, a checksum may be employed at the block level, since virtual slide images are so large that computing a checksum on the entire image would be impractical. Other forms of validation or security at the block level may also be employed. The header preferably contains file information and a reference to the baseline image 270, which contains the virtual slide image in its native resolution as received from the line scanner device. In one embodiment, the baseline image 270 is followed in the file by a thumbnail image 280, which contains a low resolution thumbnail image of the entire virtual slide. Similarly, the thumbnail image 280 is followed in the file by intermediate image level 290, then by another intermediate level 291, and so on for all intermediate images created from the base level.

The baseline image 270 and the intermediate level images 290, 291 are organized as a sequence of blocks to facilitate random access. Individual blocks may be compressed. Preferably, blocks are compressed according to the JPEG2000 standard. Alternatively, or in addition, individual blocks may be compressed according to the JPEG standard, or with LZW (lossless) encoding. Additionally, individual blocks may also contain a checksum used to verify image integrity, and/or may contain a measure of the image fidelity after compression, such as average root mean square ("RMS") or root mean cube ("RMC") distance from the original uncompressed image data.

In one embodiment, the virtual slide image file format conforms substantially to the file format set forth in the Final TIFF standard, Revision 6.0 published on Jun. 3, 1992, which is incorporated herein by reference in its entirety.

Figure 4B:
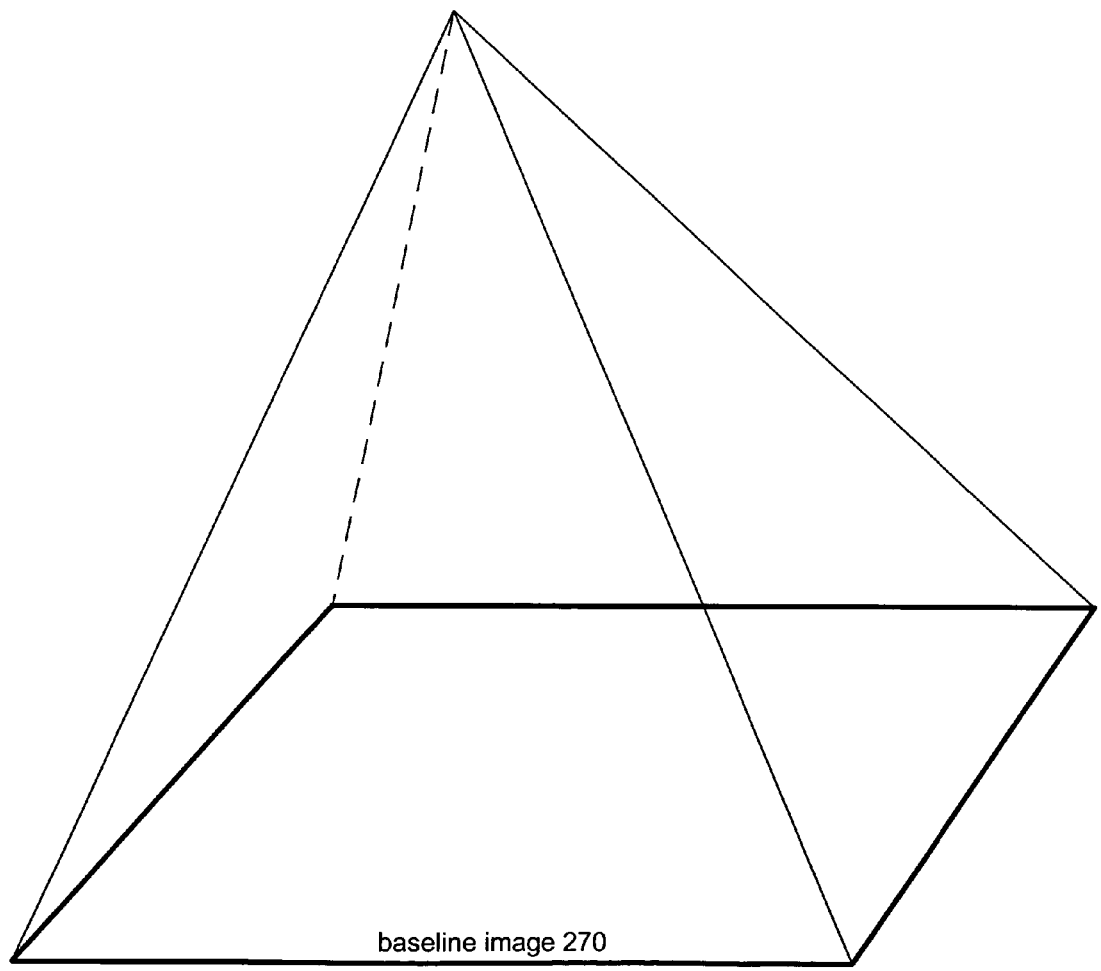
FIGS. 4B-F are block diagrams illustrating an example virtual slide file format with various resolution levels according to an embodiment of the present invention.
Figure 4C:
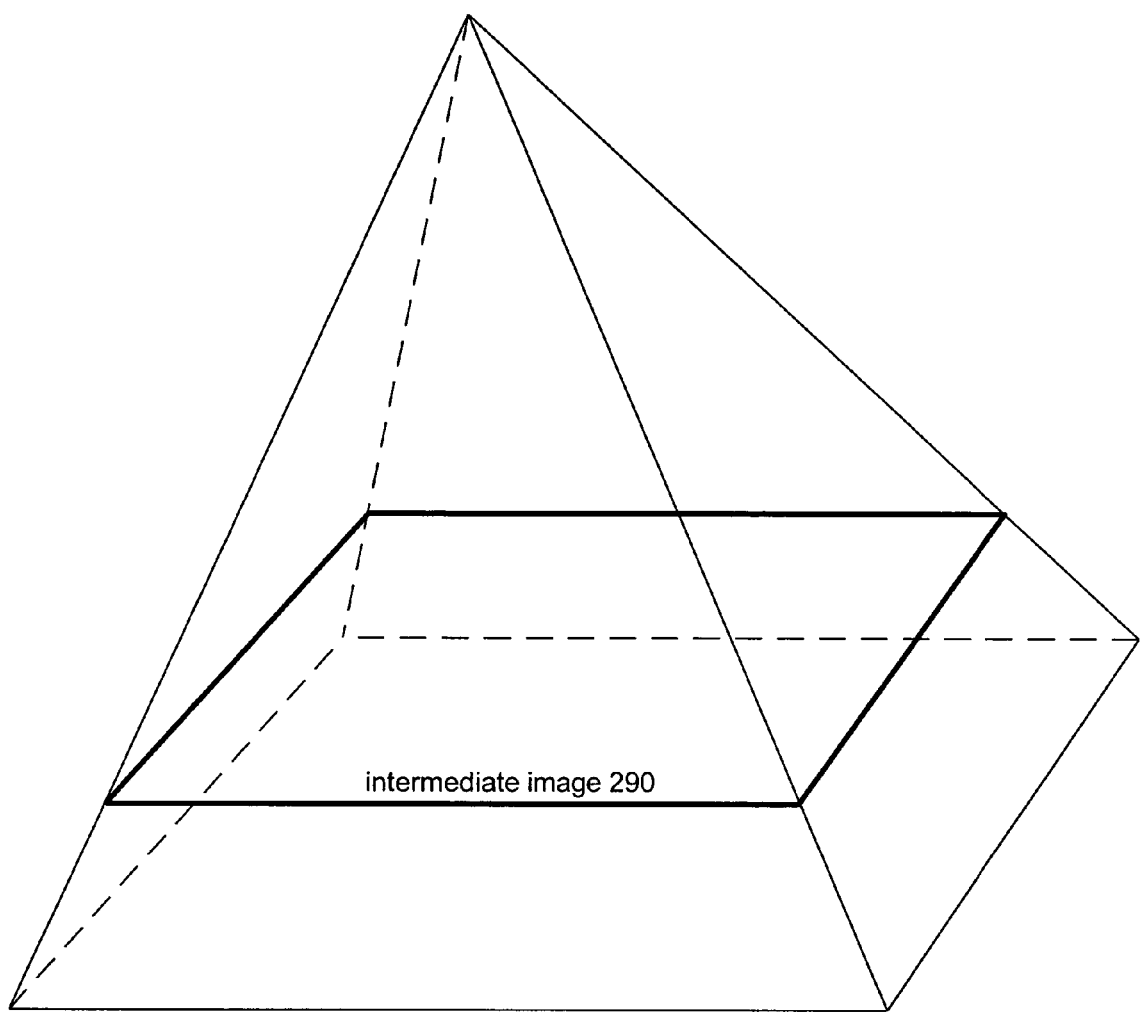
Figure 4D:
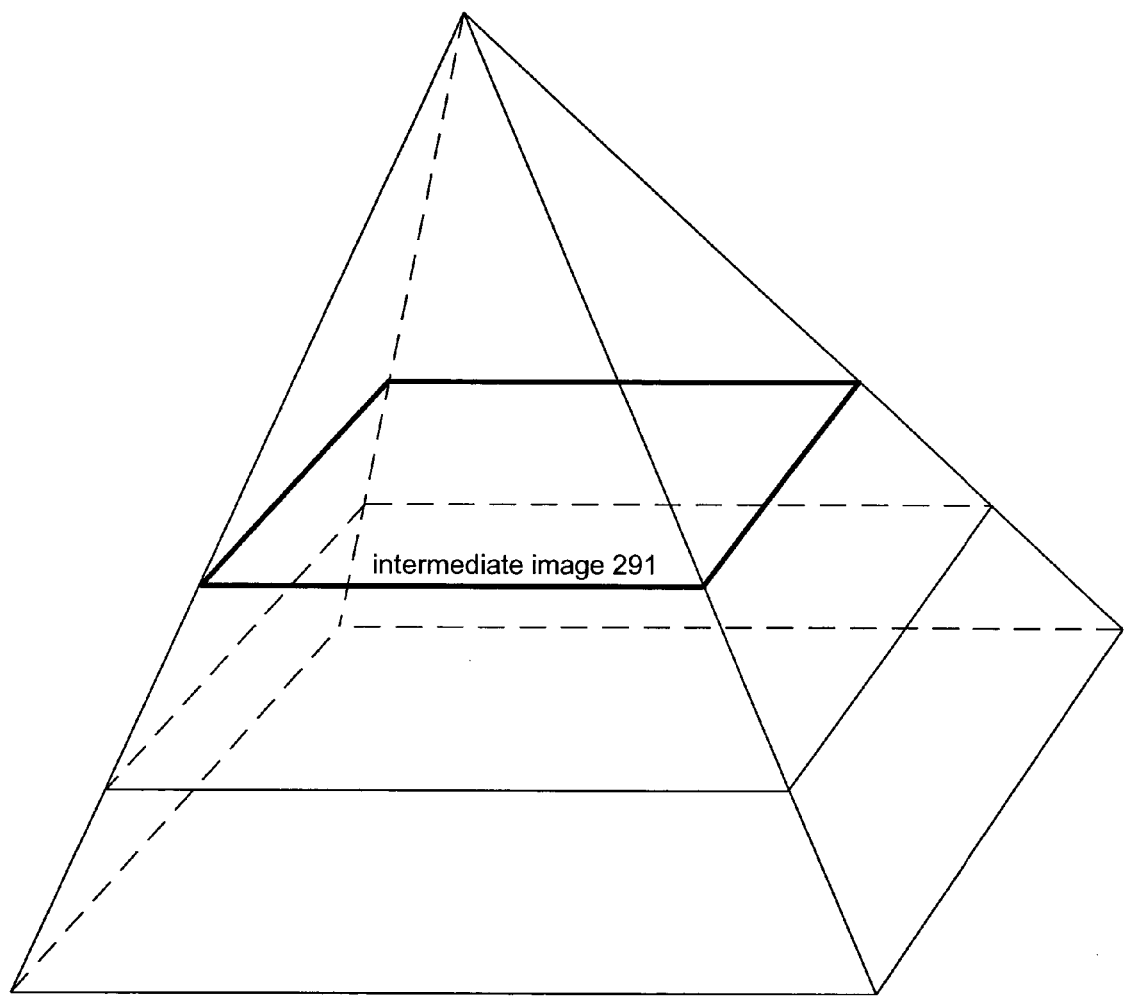
Figure 4E:
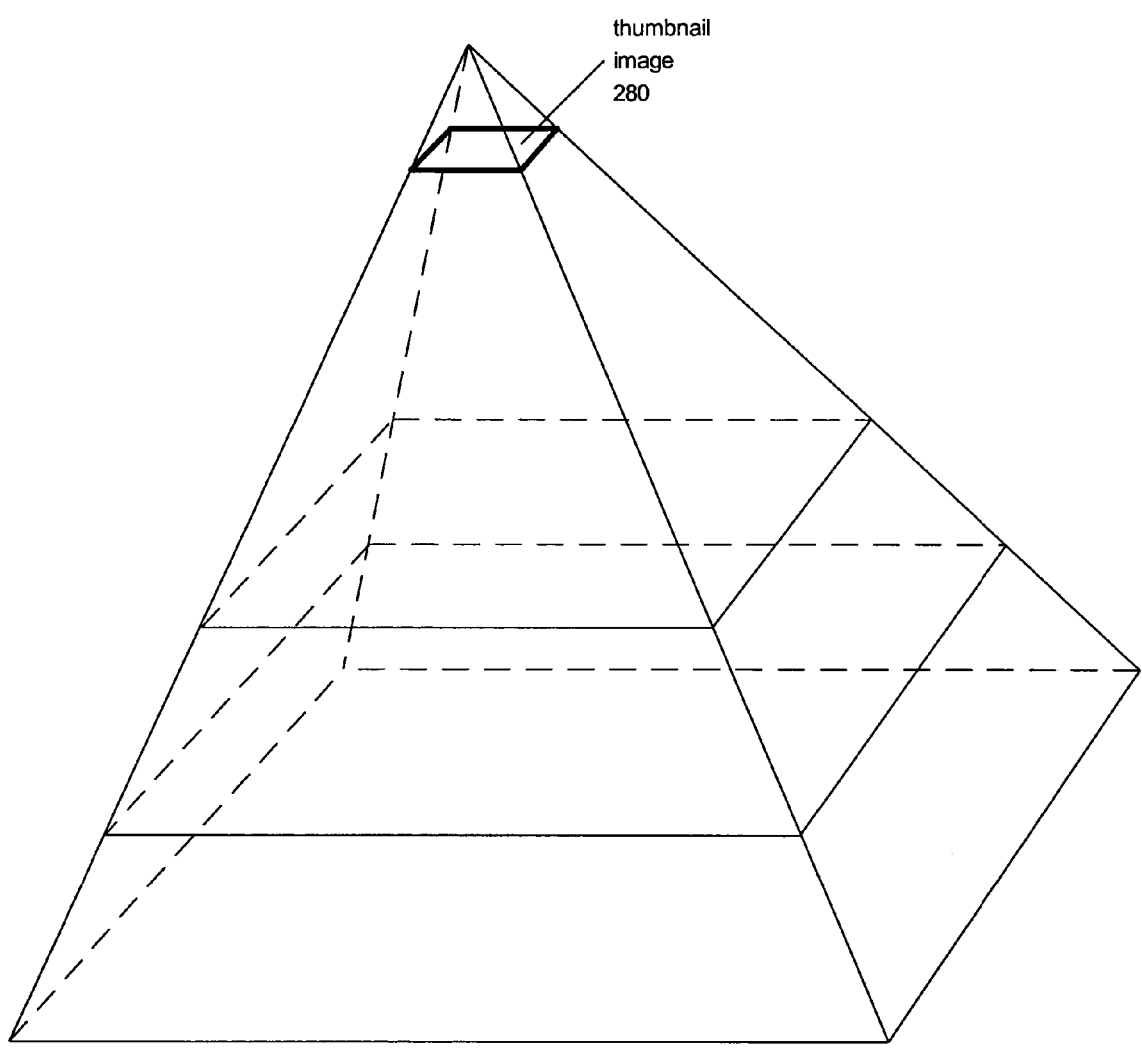

FIGS. 4B-F are block diagrams illustrating an example virtual slide file format with various resolution levels included in the file according to an embodiment of the present invention. As can be envisioned, when stacked vertically, the various levels of the baseline image in decreasing resolution order form a pyramid. At the base of the pyramid is the baseline image 270, as illustrated in FIG. 4B. The next level up, shown in FIG. 4C, is intermediate image 290. Intermediate image 290 is the virtual slide image that is closest to the baseline resolution of all of the other resolution levels in the virtual slide. FIG. 4D shows a second intermediate level image 291 placed above the baseline image and first intermediate level image in the pyramid. Any number of intermediate images may be included. For example, in one embodiment successive intermediate images are each ¼ the resolution of the preceding image. Finally, in FIG. 4E, the thumbnail image 280 tops off the pyramid of images that make up the virtual slide image file. Advantageously, the various levels of resolution and their corresponding images in the virtual slide file provide for more efficient zooming through resolution levels when viewing the virtual slide.

Figure 4F:
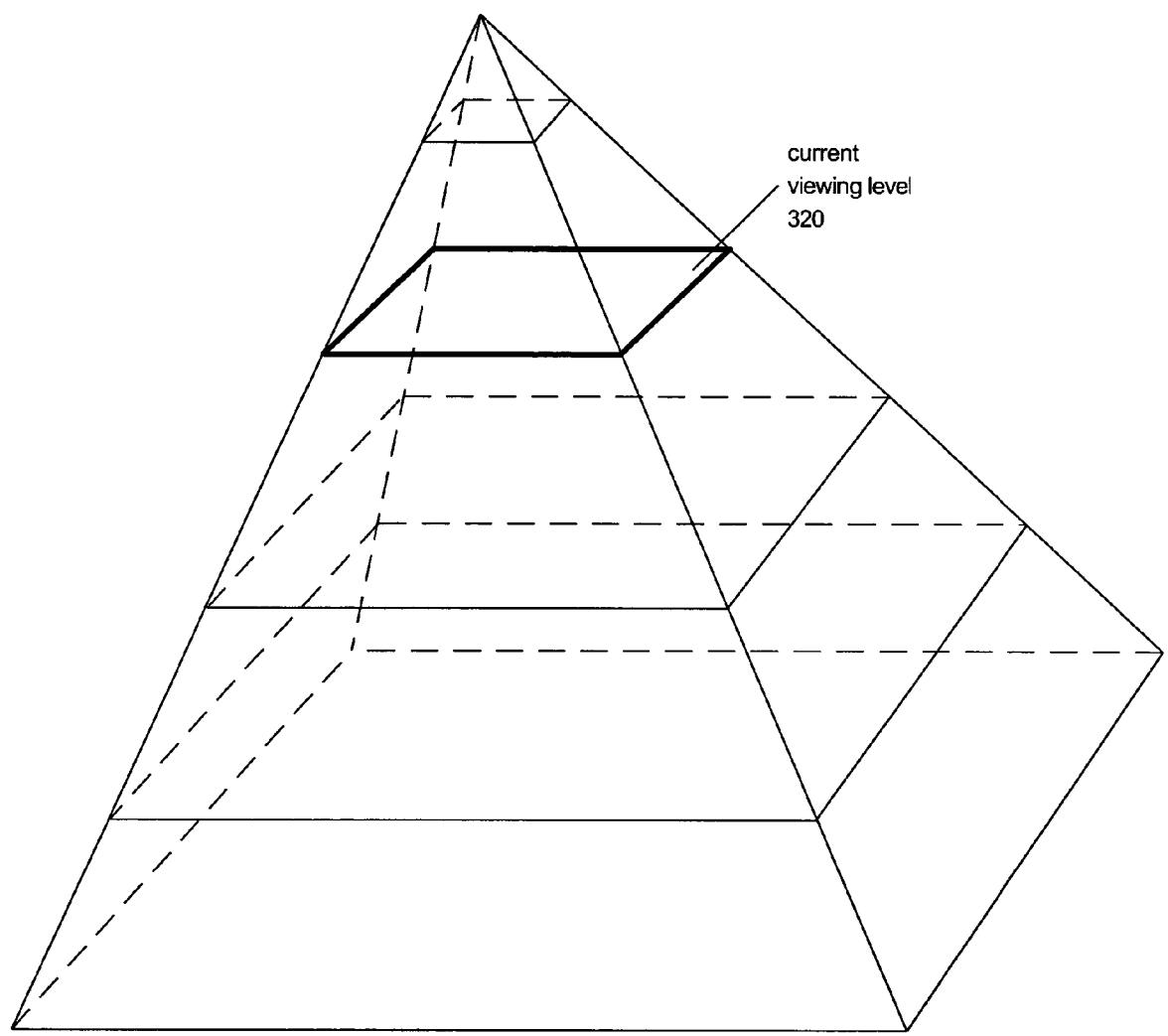

For example, FIG. 4F shows a current viewing level 320, which is between the second intermediate level image 291 and the thumbnail image 280. In one embodiment, when a viewer selects to view the virtual slide at the resolution of the current viewing level 320, the virtual slide server can provide the client viewer one or more blocks from the second intermediate level image 291 and the client viewer can scale these down to the resolution of the current viewing level. In another embodiment, when a viewer selects to view the virtual slide at the resolution of the current viewing level 320, the virtual slide server can provide the client viewer the lower resolution level image and the client viewer can scale this up to the resolution of the current viewing level. Preferably, the higher resolution image is scaled down in order to preserve image fidelity. Alternatively, the virtual slide server can perform the inter-level interpolation. In one embodiment, after an intermediate level has been interpolated, that new level can be added to the viewer or server cache to further improve the rapid zooming through various resolution levels of the virtual slide. In certain circumstances, it may be more efficient to interpret a current viewing level a second or subsequent time, as needed, rather than store the current viewing to disk after the first rendering and then later retrieve the stored image for a second or subsequent viewing.

Figure 4G:
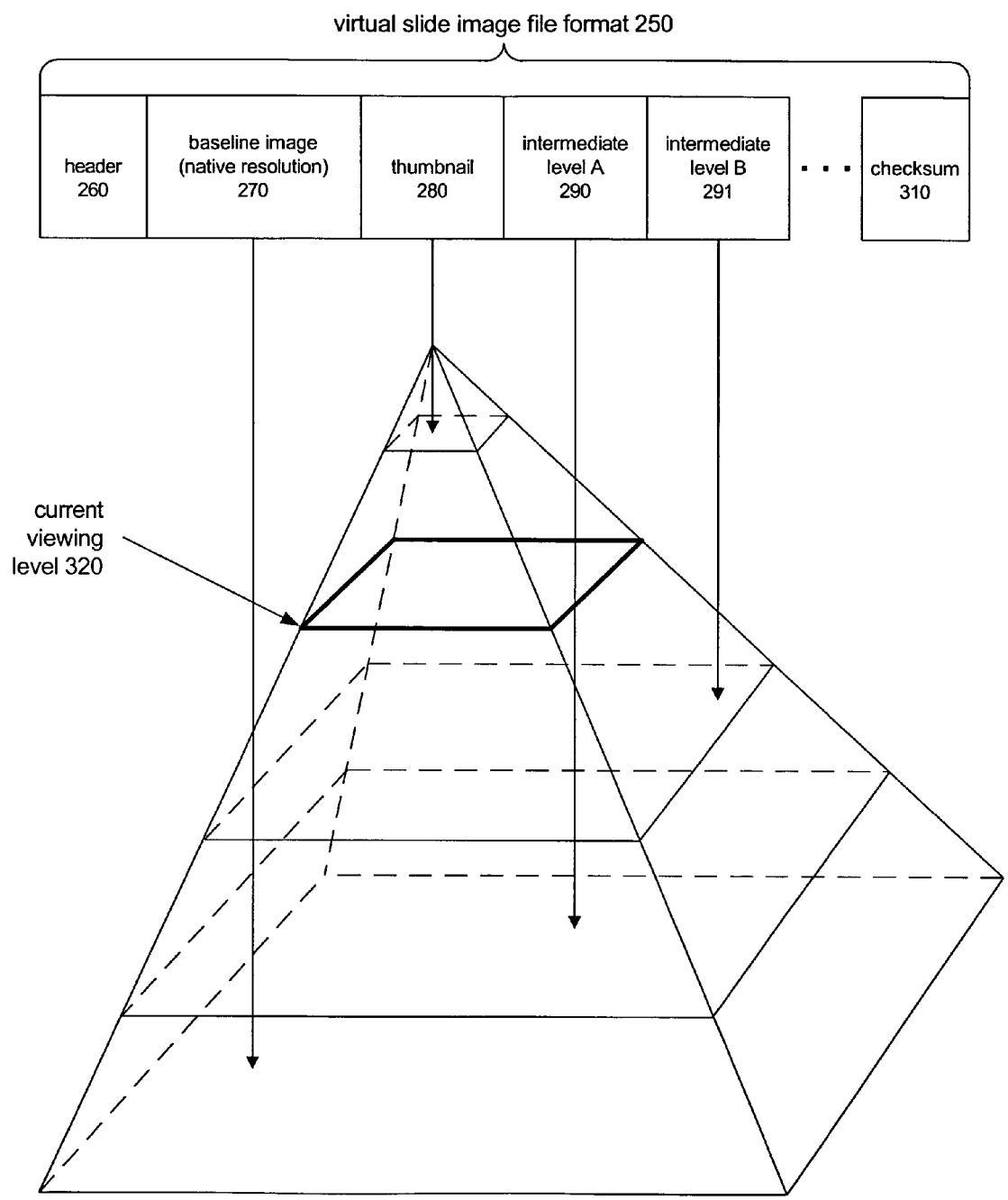
FIG. 4G is a block diagram illustrating an example virtual slide file format in connection with various resolution levels according to an embodiment of the present invention.

FIG. 4G is a block diagram illustrating an example virtual slide file format in connection with various resolution levels according to an embodiment of the present invention.

Figure 5A:
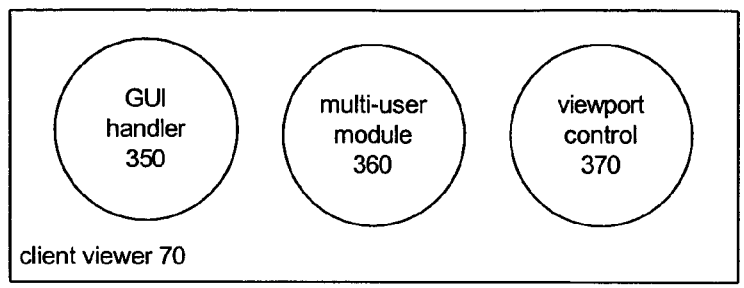
FIG. 5A is a block diagram illustrating an example client viewer according to an embodiment of the present invention.

FIG. 5A is a block diagram illustrating an example client viewer 70 according to an embodiment of the present invention. The client viewer 70 is an application that runs on a remote device that is communicatively connected with the virtual slide server via a network, or perhaps a direct connection such as a computer cable. In the illustrated embodiment, the client viewer 70 comprises a graphical user interface ("GUI") handler 350, a virtual microscopy conferencing ("VMC") module 360, and a viewport control 370.

The GUI handler 350 manages the display of windows and content for those windows on the viewing device. Additionally, the GUI handler 350 manages all keyboard and mouse input to the client viewer 70. The VMC module 360 is used for virtual microscopy conferencing sessions that are later described in detail with respect to FIGS. 7A-7B. The viewport control 370 manages all interactions with a virtual slide, either via direct access to a local virtual slide file, or via remote access to a virtual slide server as described above.

Figure 5B:
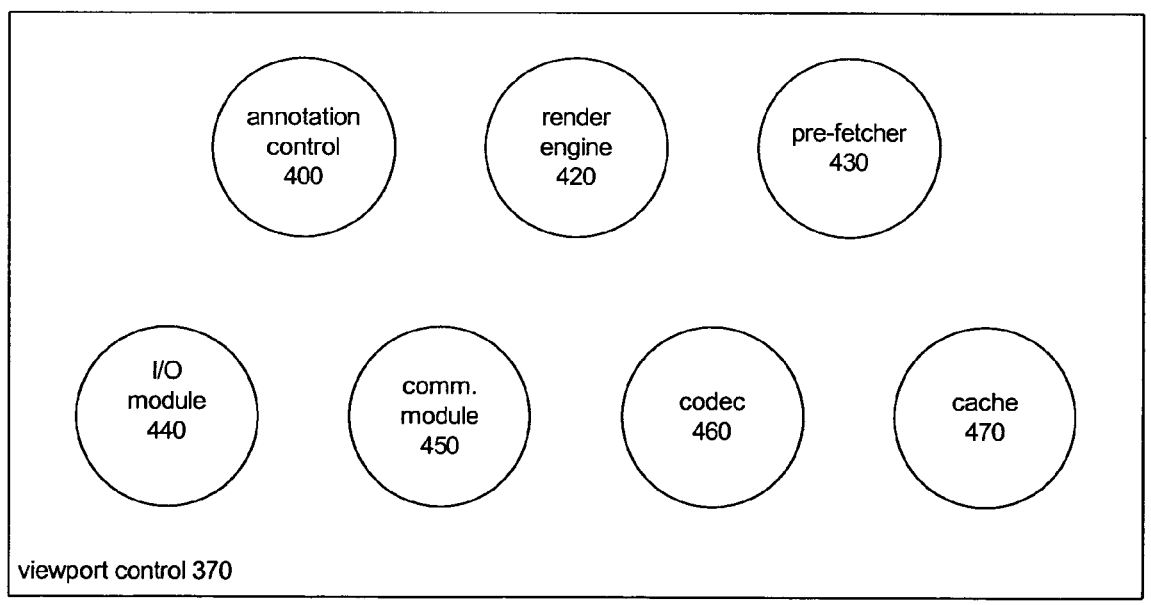
FIG. 5B is a block diagram illustrating an example viewport control according to an embodiment of the present invention.

FIG. 5B is a block diagram illustrating an example viewport control 370 according to an embodiment of the present invention. In the illustrated embodiment, the viewport control comprises annotation control 400, a render engine 420, a pre-fetcher 430, an I/O module 440, a communication module 450, one or more codecs 460, and a cache 470.

The annotation control 400 handles annotation requests including adding new annotations, deleting annotations, and presenting the various annotation layers. The render engine 420 manages the display and manipulation of virtual slide image data. The render engine 420 is configured to use cached image data to provide the best possible view of a virtual slide image at any location within the virtual slide, any dimension, and any resolution. As more data is received from the virtual slide server, the render engine 420 advantageously updates the currently displayed image to improve the image.

The pre-fetcher 430 dynamically fetches image data for virtual slides in anticipation of requests from the render engine 420. The pre-fetcher 430 tracks user navigation movements within the virtual slide displayed by viewport control 370 and determines a particular direction of motion for the virtual slide image. Accordingly, the pre-fetcher 430 fetches image data according to the slide direction of motion and anticipates image data requested by the render engine 420.

The I/O module 440 handles all requests for virtual slide data from the local data storage area (not shown). Advantageously, the local client viewer can store image data locally to allow standalone viewing of virtual slides. These images are preferably stored in a local data storage area that is accessible to the I/O module 440. The communication module 450 handles network communications with the virtual slide server. Preferably, the communication module 450 works with the pre-fetcher 430, the render engine 420 and other components of the viewport control 370 and client viewer to access data and information from the virtual slide server. Additionally, the communication module 450 preferably works with the annotation control 400 to provide new annotations, modifications, and deletions to annotations with the virtual slide server.

Additionally, the viewport control comprises one or more codecs 460 that are preferably configured to implement various different compression and decompression techniques. In a preferred embodiment JPEG2000 compression is employed for virtual slide image files and therefore a codec 460 is configured to compress and decompress according to the JPEG2000 standard. Additionally, a codec 460 may be configured to also compress and decompress according to the JPEG and Lempel-Ziv Welch ("LZW") compression standards. The viewport control may support multiple compression technologies concurrently, in which case there will be multiple instances of codec 460, selected based on image attributes.

Finally, the viewport control comprises a cache 470. The cache 470 may be implemented as a single physical cache or as a plurality of separate physical caches. In one embodiment, several logically discrete caches are used by the viewport control 370 including a block cache, a sub-region cache, and a virtual slide information cache. The I/O module 440 checks the appropriate cache 470 for block and/or image data prior to retrieving data from a local disk or remote server, and updates the cache with newly retrieved data.

Figure 5C:
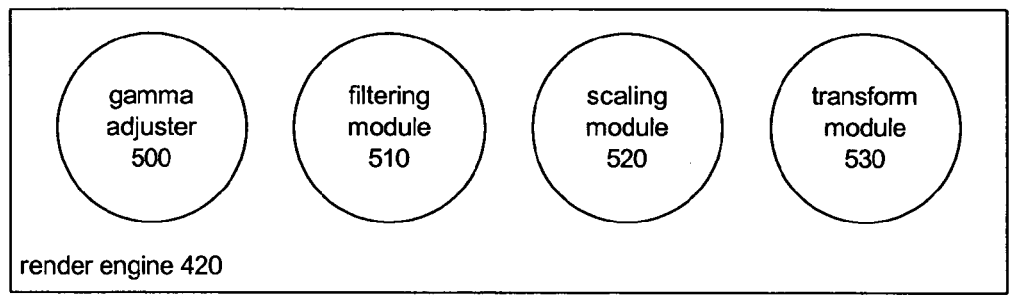
FIG. 5C is a block diagram illustrating an example render engine according to an embodiment of the present invention.

FIG. 5C is a block diagram illustrating an example render engine 420 according to an embodiment of the present invention. The render engine 420 is the primary component of the viewport control and comprises a gamma adjuster 500, a filtering module 510, a scaling module 520, and a transform module 530.

The gamma adjuster 500 provides real time adjustment of the color mapping of red-green-blue ("RGB") values in image data to the actual pixels being displayed on a monitor. An advantage of this capability is that it allows compensation for the difference in ambient light and monitor characteristics when virtual slides are viewed. The filtering module 510 enables filtering of virtual slide image data by applying predefined or user-specified convolution matrices to image data, providing contrast enhancement, edge sharpening, and other image processing capabilities.

The scaling module 520 allows the resolution of the virtual slide image to be increased or decreased with little loss of image fidelity. Advantageously, the time required for scaling is significantly reduced by pre-populating a virtual slide image file with various intermediate level resolution images 290, 291. The transform module 530 allows virtual slide images to be rotated in an orthogonal fashion such that 90 degree rotations and horizontal and vertical flips of the image can be accomplished.

Figure 5D:
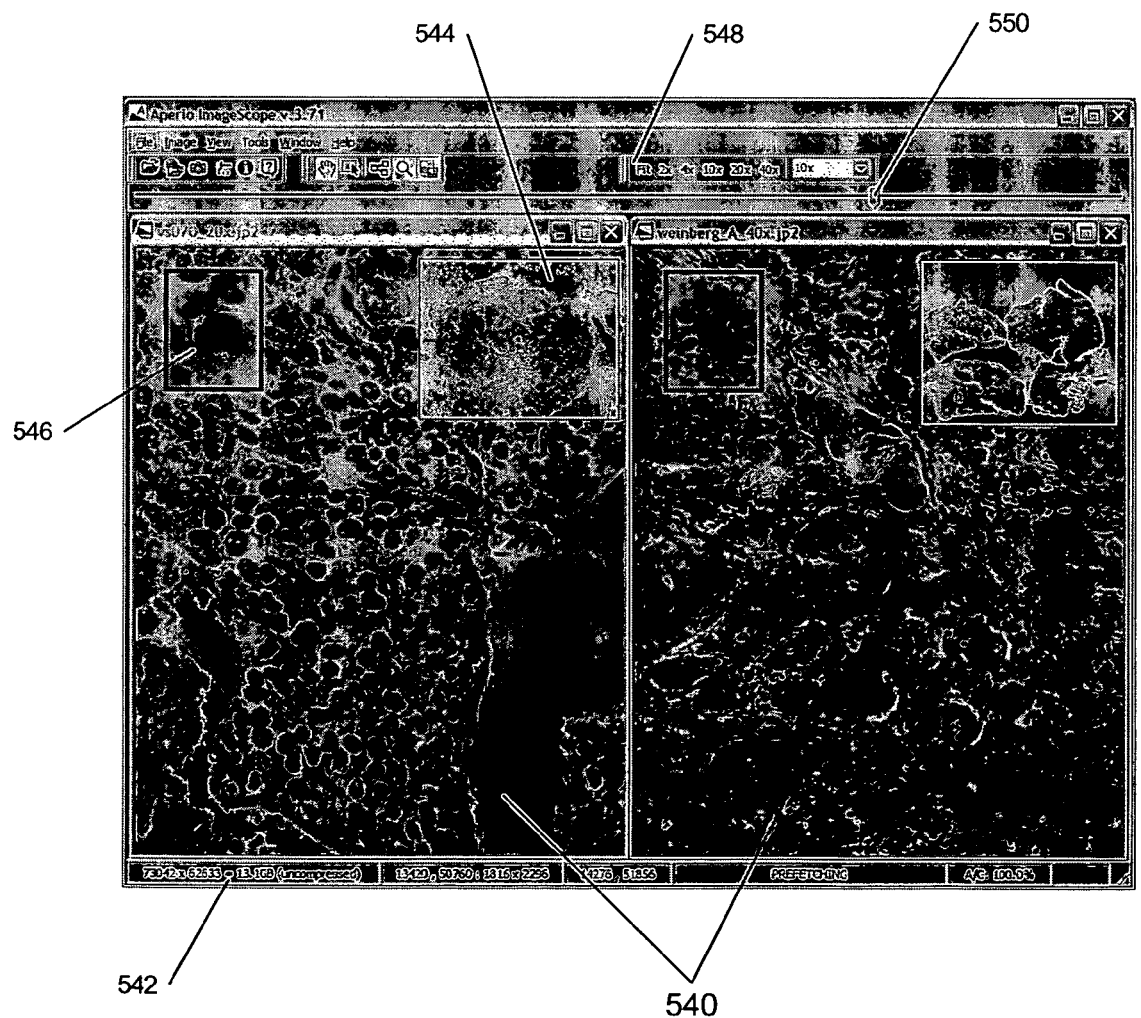

FIG. 5D-H are screen shots illustrating example viewing windows and manipulation control windows according to an embodiment of the present invention. FIG. 5D illustrates an example client viewer window. The window is divided into two viewports 540, which are each displaying an image of a separate slide. The viewport 540 on the right is the active window and information about the window is shown in the status bar 542. The status bar indicates that the image is 73,042×62,633 pixels, which is about 13.1 GB of image data for the virtual slide. The status bar also indicates that the viewport 540 is currently pre-fetching data.

Additionally, each viewport 540 shows a thumbnail image for the entire virtual slide such as thumbnail image 544. Advantageously, clicking or dragging the mouse in the thumbnail image causes the scaled image in the viewport window to be positioned accordingly. Furthermore, rectangles are present in the thumbnail image to show the relative position and size of the current view.

A magnifier window 546 may also be opened up in each viewport 540. The magnifier window 546 advantageously displays the region surrounding the cursor at 2× the relative magnification. Dragging the mouse causes the magnified area surrounding the mouse to move. Advantageously, images can be scaled beyond the scanned resolution level to provide a viewer (i.e., person) with more information due to the small size of pixels on a computer screen. The magnifier window 546 allows a user to sweep over the displayed image data to provide 2× additional resolution. This additional resolution is also available for the baseline image.

A toolbar 548 is also provided that allows the resolution of each viewport window to be set at a particular predetermined resolution. Advantageously, the predetermined resolutions may directly correspond with the baseline and intermediate levels already present in the virtual slide image file. Finally, a zoom slider 550 allows for the selection of any level of resolution and further allows rapid zooming in and out on the virtual slide image in the viewport control.

FIG. 5E illustrates an example gamma adjustment window. Various tabs are available for adjusting the brightness/contrast of the image, the color balance of the image, the color curves of the image, and loading and saving the adjustment settings. The color curves tab is shown in the illustrated embodiment. Color curve 552 allows a user to adjust the color mapping along a spectrum. The color boxes on the left allow the user to select the curve for a particular color channel to be modified independently or to select all color channels to be modified simultaneously.

FIG. 5F illustrates an example filtering window. The top portion of the window lists several pre-defined filters that can be applied by selecting the desired radio button. Additionally, a custom 5×5 convolution matrix may be defined by entering the appropriate values in the dialog box input fields 556. Convolution matrices enable contrast enhancement, edge enhancement, and other image processing functions.

FIG. 5G illustrates an example transformation window. The transformation window allows a user to rotate a virtual slide image 90 degrees or mirror flip the image across a horizontal or vertical center line by selecting the desired radio button.

Figure 5H:
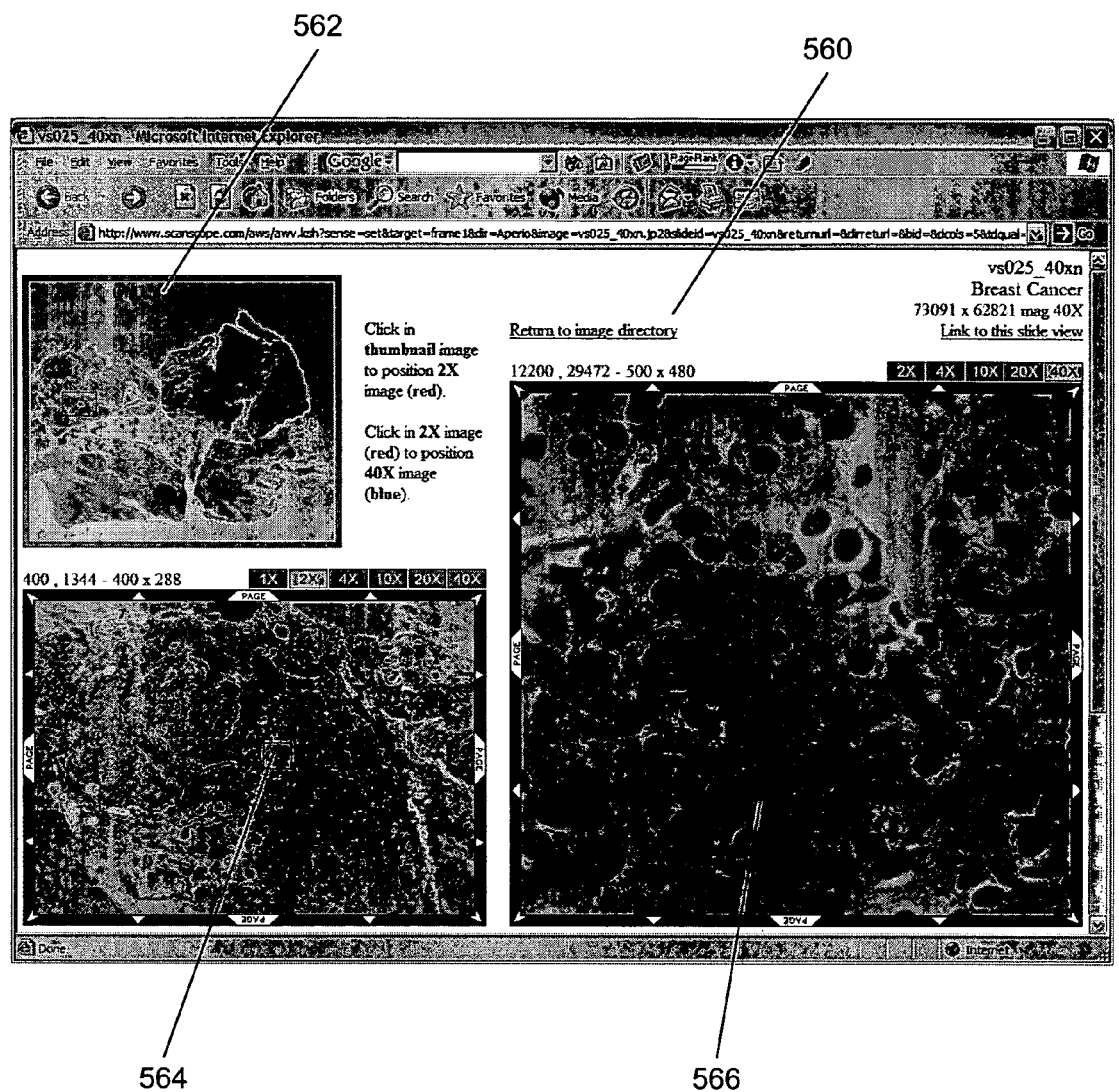

FIG. 5H illustrates an example web viewer window. The web viewer window is made up of HTML and embedded images. Standard text 560 can be displayed and arranged as desired and is generated by the web viewer as previously described with respect to FIG. 3. A thumbnail image 562 is also provided, with an internal size and location reference for orientation of the intermediate resolution image 564. Additionally, within the intermediate resolution image 564, a similar reference is provided that indicates the current location position of the high resolution image 566.

Figure 6A:
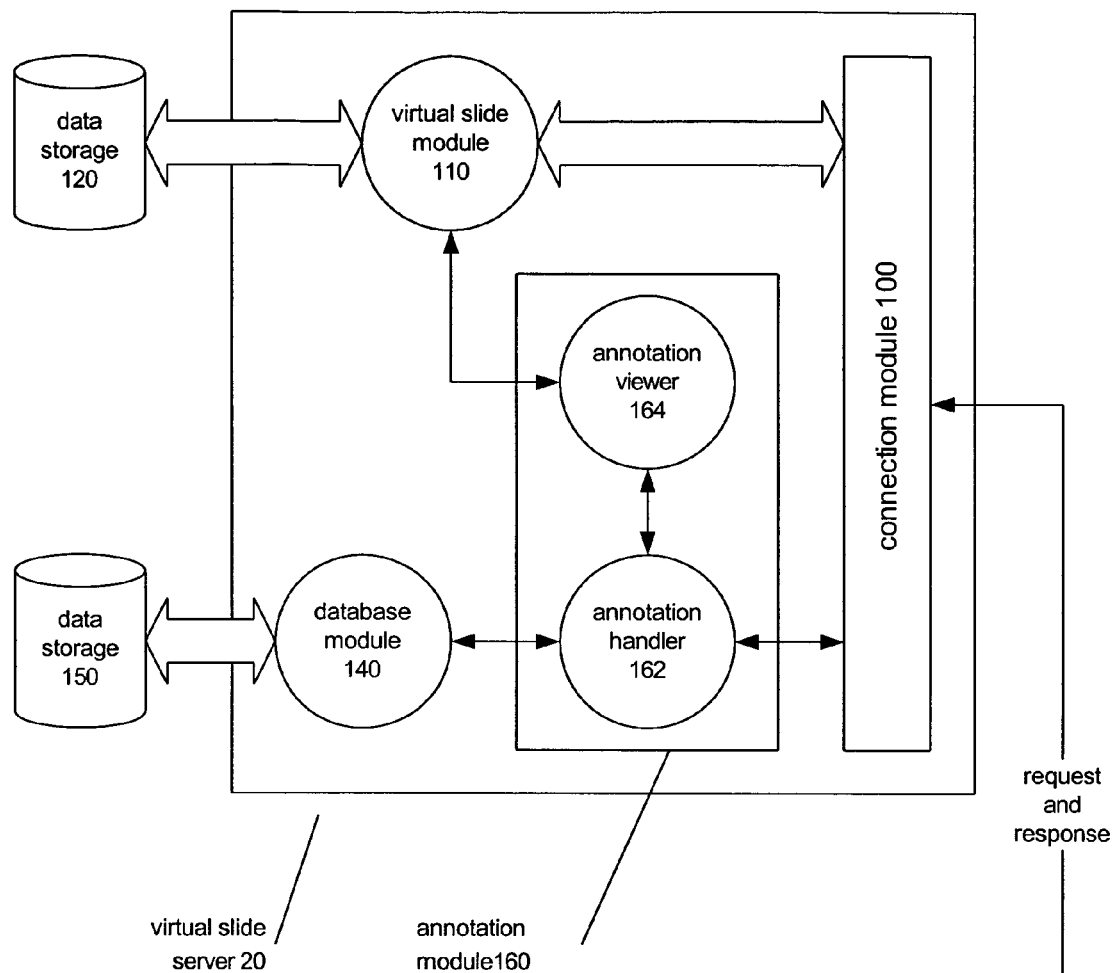
FIG. 6A is a block diagram illustrating an example annotation module according to an embodiment of the present invention.
Figure 6A:
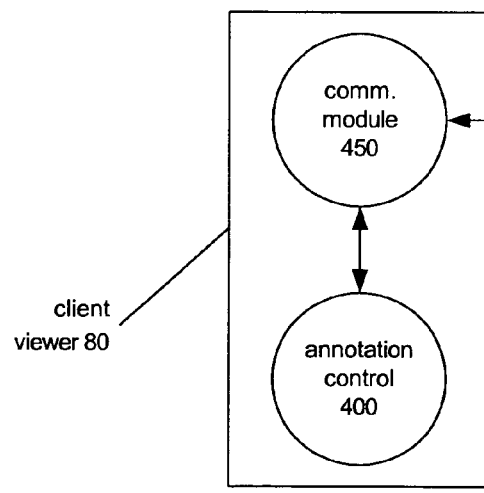

FIG. 6A is a block diagram illustrating an example annotation module 160 according to an embodiment of the present invention. The annotation module 160 comprises an annotation viewer 164 and an annotation handler 162. The annotation viewer 164 works in conjunction with the virtual slide module 110 to provide annotation information (i.e., layers) for display over the top of the virtual slide image data. Annotation handler 162 processes annotation creation, editing, and deletion requests from viewers such as client viewer 80. Annotation handler 162 additionally manages the maintenance of annotation information in the data storage area 150 and fetches the annotation data, where appropriate, and provides the annotation information to the annotation viewer 164.

In one embodiment the user at a client viewer 80 may create an annotation, for example, using the annotation control 400. The annotation information is sent by the communication module 450 at the client viewer 80 to the virtual slide server 20. The request comprising the annotation creation is processed by the communication module 100 and passed to the annotation handler 162. The annotation handler 162 then provides the annotation to the database module 140 for storage in data storage area 150.

Figure 6B:
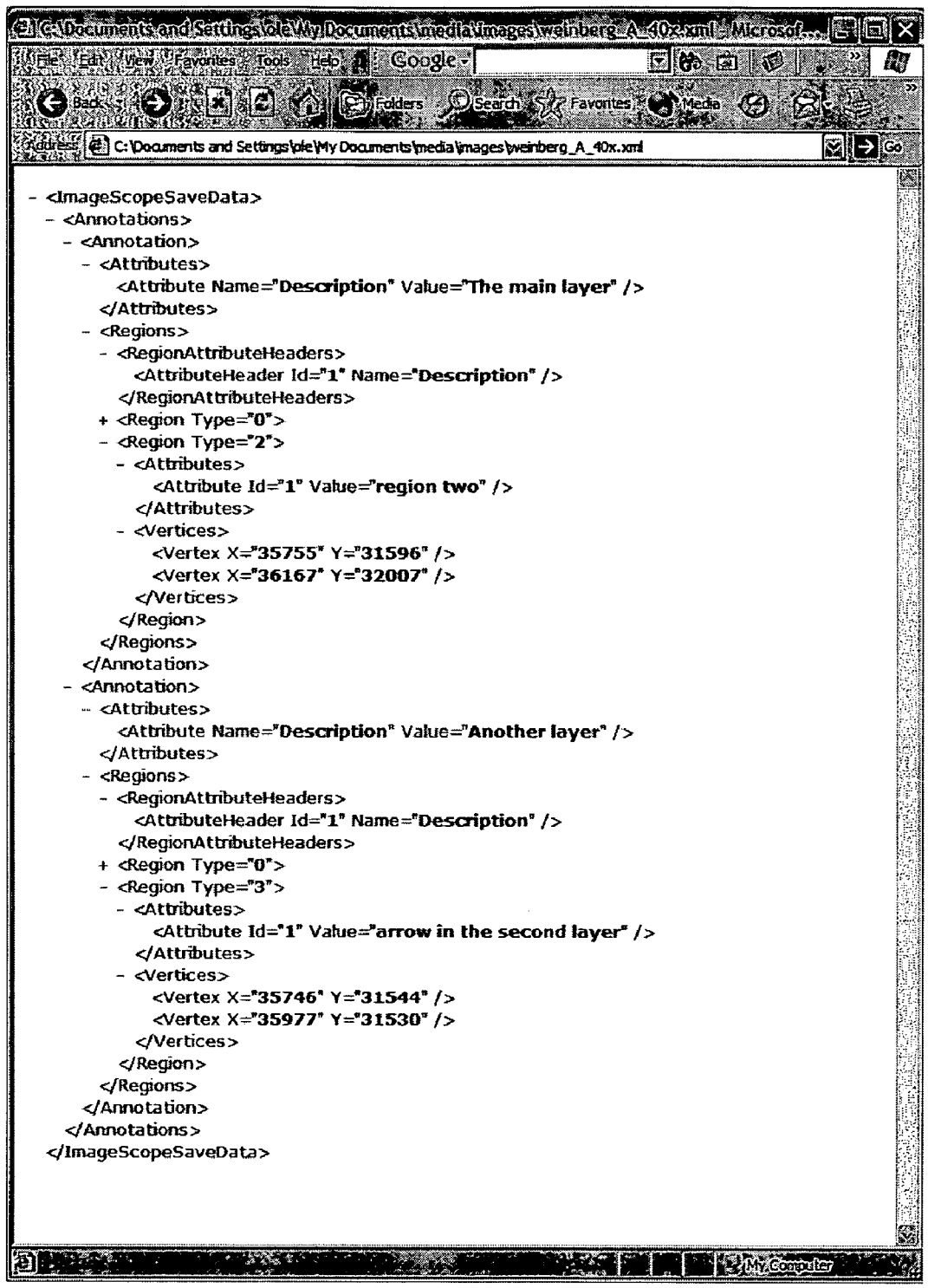
FIGS. 6B-C are screen shots illustrating example annotations according to an embodiment of the present invention.
Figure 6C:
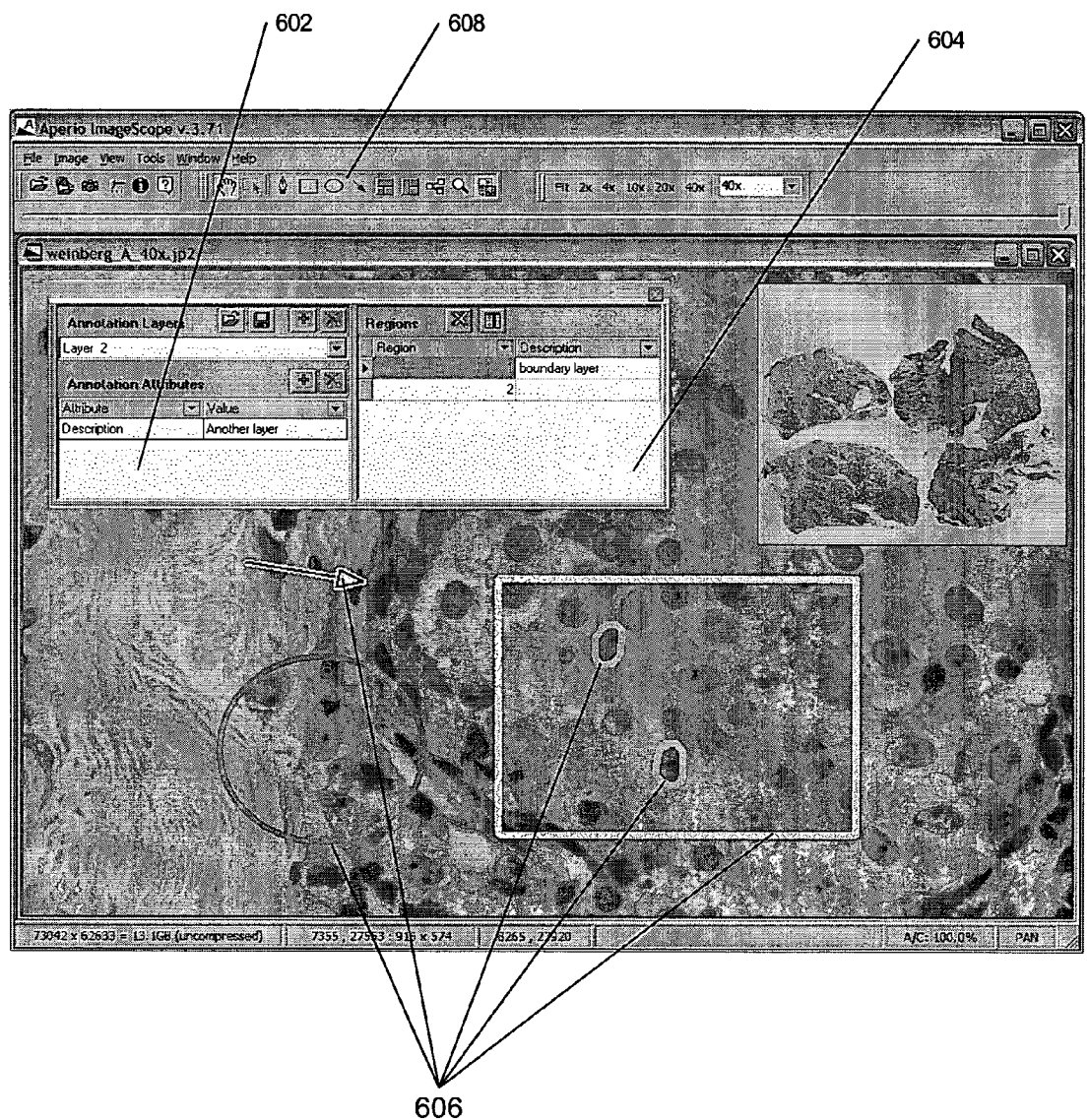

FIGS. 6B-C are screen shots illustrating example annotations according to an embodiment of the present invention. FIG. 6B illustrates an example annotation in a structured language. In the illustrated embodiment, the annotation is shown in the extensible markup language ("XML"), although other structured languages may also be employed. Advantageously, such an annotation can be stored in a database as a simple string, as will be understood by those having skill in the art.

Annotations are described, stored, and retrieved using coordinates relative to the virtual slide's base resolution level. This enables annotations to be scaled to any resolution level along with the image data they describe. In the illustrated embodiment, annotations consist of one or more displayed features or regions, which are grouped into layers. In one embodiment, individual annotation layers may be selectively enabled or disabled.

FIG. 6C illustrates an example viewport window with annotations. A floating dialog box 602 provides annotation control to the user and facilitates the selection of an annotation layer and layer attributes. Similarly, dialog box 604 provides the user with the ability to add, edit, and delete individual annotations and annotation attributes within the current layer.

Individual annotations 606 may embody a variety of different forms such as an ellipse, an arrow, free-form polygons, and rectangles, just to name a few. In one embodiment each annotation in a particular layer is displayed in a different color, for example, with the currently selected annotation having a black outline. Annotation authoring tools appear on a menu bar 608 and may include a pen tool, a shape tool (for rectangles and ellipses), and an arrow tool, just to name a few.

In one embodiment, annotations are composed of an annotation region, which is associated with a particular location relative to the baseline image in the virtual slide. Various values can be established with respect to each annotation region and can be stored in the form of key=value in the annotation string. An annotation layer may have multiple annotation regions. Annotation layers may also have various values associated with the layer, for example, in the form of key=value and stored along with the annotation string.

Figure 7A:
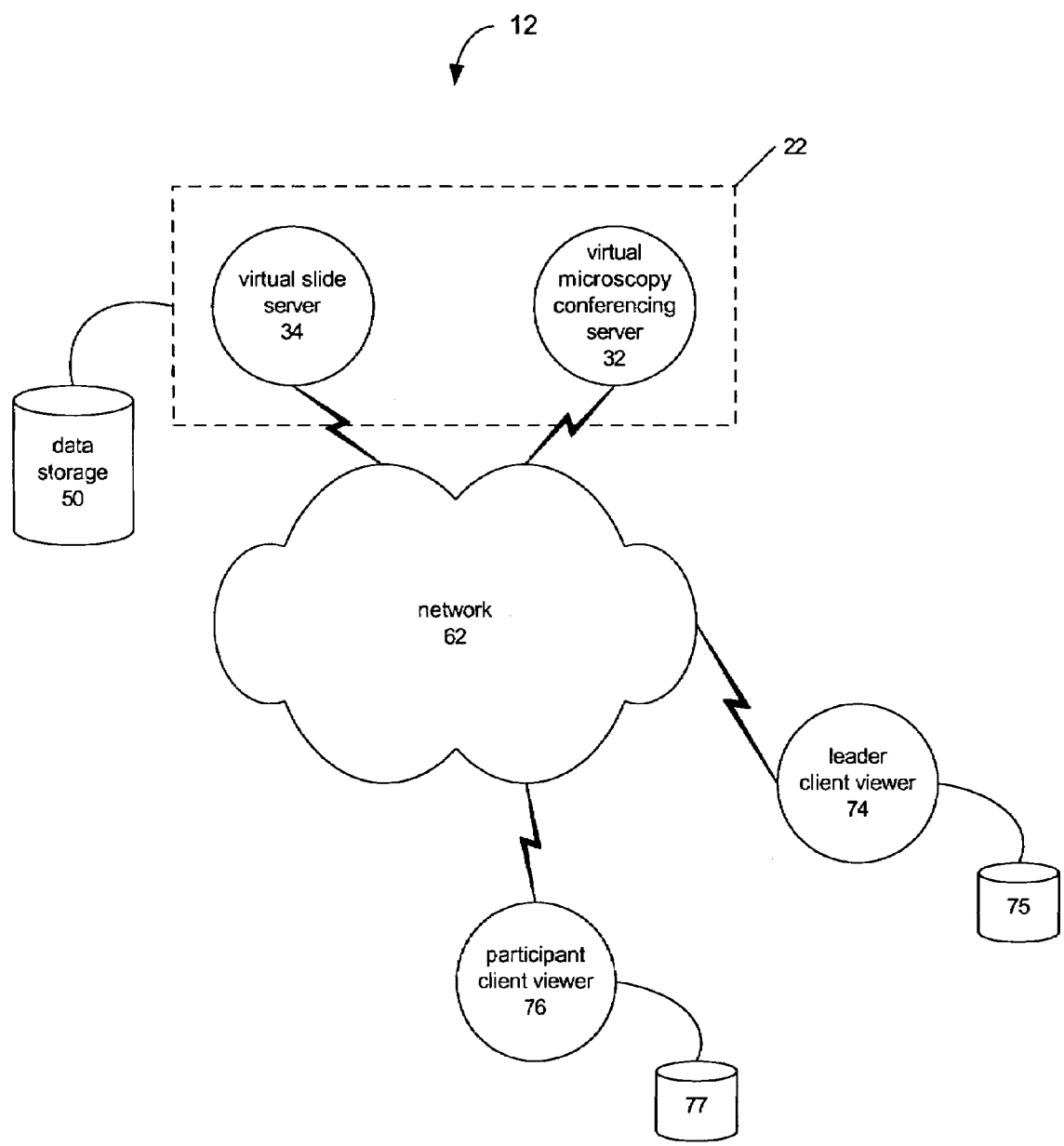
FIG. 7A is a network diagram illustrating an example virtual microscopy conferencing viewing system according to an embodiment of the present invention.

FIG. 7A is a network diagram illustrating an example VMC viewing system 12 according to an embodiment of the present invention. In the illustrated embodiment, the VMC server 32 is communicatively coupled with a leader client viewer 74 and a participant client viewer 76 over a network 62. In one embodiment, there may be multiple participant client viewers 76, but only one leader client viewer 74 per conferencing session. The leader client viewer 74 may be configured with a local data storage area 75 and each participant client viewer 76 may be similarly configured with a local data storage area 77. In an alternative embodiment, there may be more than one leader client viewer 74.

As illustrated by FIG. 7A, in one embodiment of the present invention a virtual slide server 34 supplies image data to all participants 74 and 76 in a virtual microscopy conferencing session, from data storage 50 or from an image cache (not shown). Optionally, the virtual slide server 34 may be co-located with the virtual microscopy conferencing server 32, and/or the servers 34 and 32 may be combined together into one shared server 21.

In virtual microscopy conferencing, the leader client viewer 74 controls the viewing session. Virtual slide commands that are received from the leader client viewer 74 cause the VMC server 32 to relay these commands to the other participant viewers in the session. For example, all pan and zoom and other interactive commands, including presentation of annotation layers and creation of annotation regions, received from the leader client viewer 74 are carried out locally and relayed to all the other participant viewers. Additionally, commands to open and close images, and other session control activities are initiated by the session leader. Participant client viewers may modify their. image display locally (panning, zooming, etc.) but these actions are not relayed through the VMC server 32 to the other session participants.

Figure 7B:
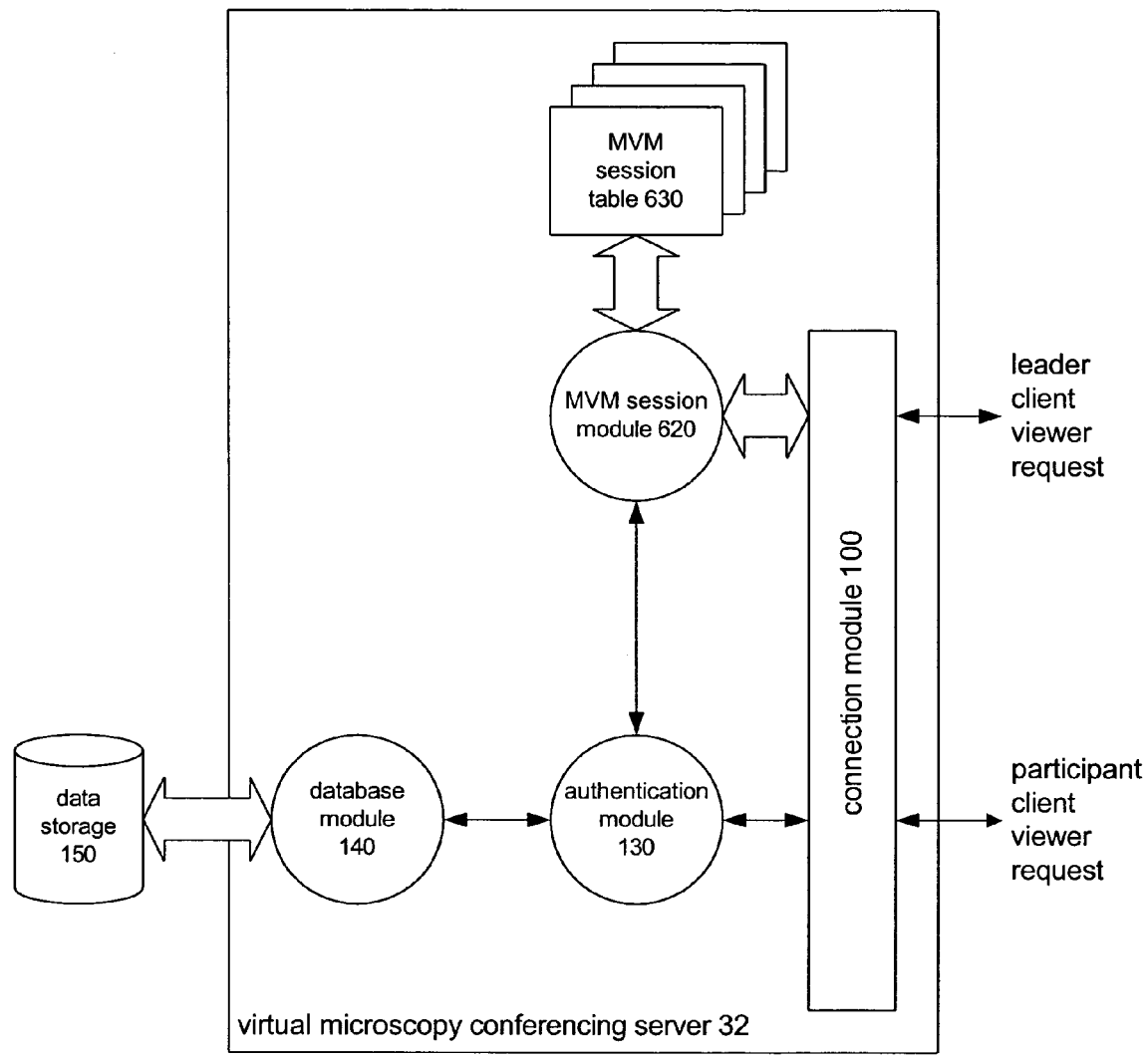
FIG. 7B is a block diagram illustrating an example virtual slide server for virtual microscopy conferencing according to an embodiment of the present invention.

FIG. 7B is a block diagram illustrating an example VMC server 32 for virtual microscopy conferencing according to an embodiment of the present invention. The VMC server 32 includes the VMC session manager 620 and the VMC session table 630. The authentication module 130 and database module 140 are used to authenticate VMC session participants.

Advantageously, the VMC session manager processes all VMC requests received from a leader client viewer. Additionally, VMC session manager 620 maintains the VMC session table 630 to keep track of which client is the leader, and to maintain a queue of clients which have requested leadership. Moreover, the VMC session table 630 preferably maintains the status of each participant client viewer in order to synchronize the current virtual slide view of each participant client viewer with that of the leader client viewer.

In one embodiment, the VMC session table 630 comprises a list of participant client viewers that have requested to become the leader client viewer. Advantageously, at any time the leader client viewer may pass session leadership to any participant client viewer, either explicitly, or implicitly by requesting that the VMC server 32 select the next participant client waiting in the session leadership queue.

The VMC session manager 620 initially receives a VMC request from a first client viewer in order to establish a session. The first client viewer becomes the leader client viewer and sets a password and session identifier. Additional client viewers that specify the session identifier and provide the correct password then become participant client viewers. In one embodiment, each participant client viewer has a unique VMC session table created to track that participant client viewer's status.

VMC session clients, including the leader 74 and all participants 76, share access to one or more virtual slide servers 34 to obtain image data, as described previously. Access to image data may be at the image block level, with processing of blocks performed by the client, or at the image sub-region level, with processing of blocks to render sub-regions performed by the server on behalf of the client.

In one embodiment gamma adjustment of virtual slide images is available on an individual participant basis. The gamma adjustment is unique to each individual monitor and ambient lighting and therefore it is advantageously controllable by each individual participant client viewer in an VMC session. Gamma adjustment operations may be performed on the virtual slide server 34 but are more typically carried out by the local client viewer.

Figure 7C:
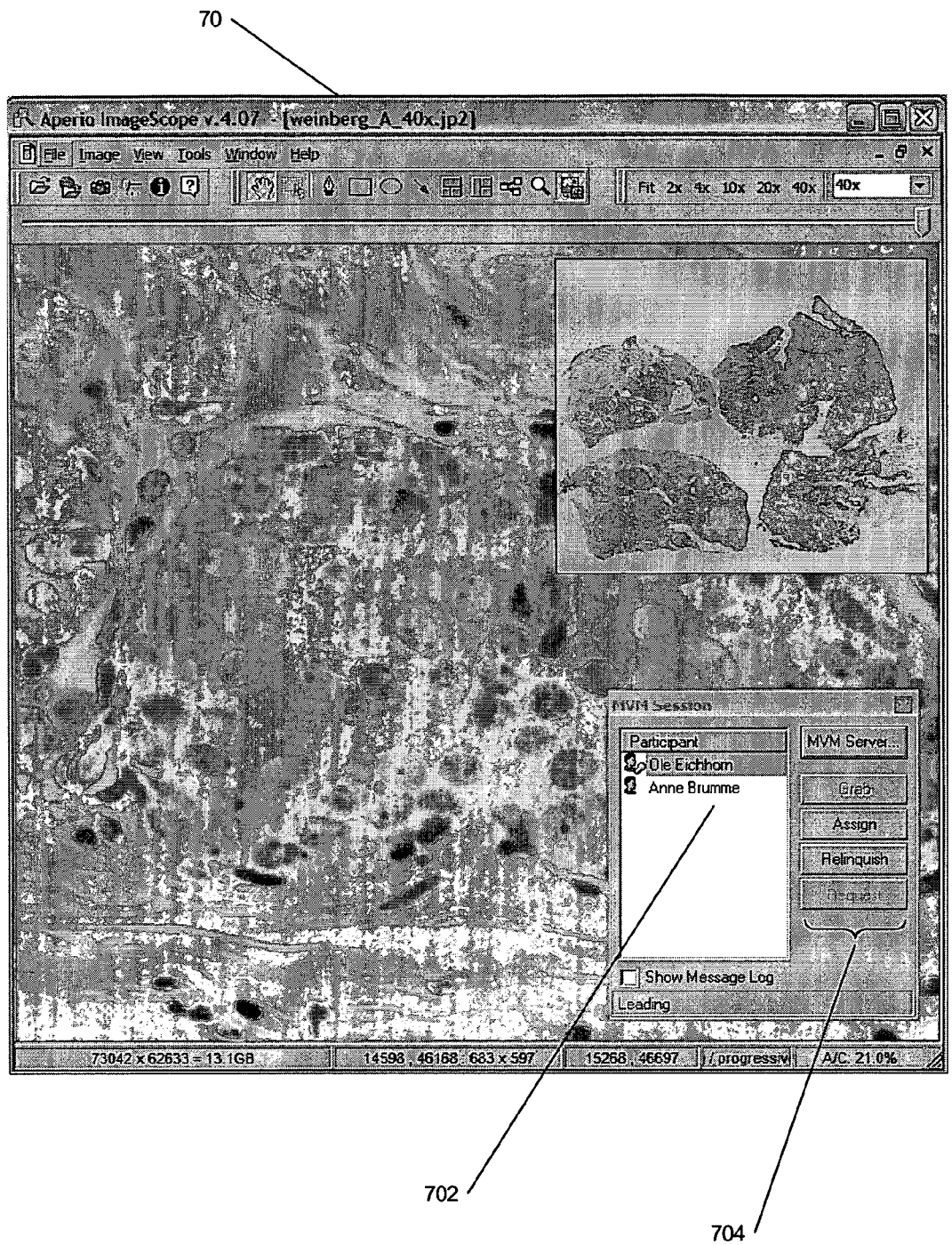
FIG. 7C illustrates an example embodiment of a virtual microscopy conferencing client according to an embodiment of the present invention.

FIG. 7C illustrates an example embodiment of a virtual microscopy conferencing client (either a leader or a participant), built into a virtual slide viewer 70. A floating dialog box displays current session status, including a list of participants 702. Controls 704 are provided to request, assign, and relinquish leadership of the session.

Figure 8A:
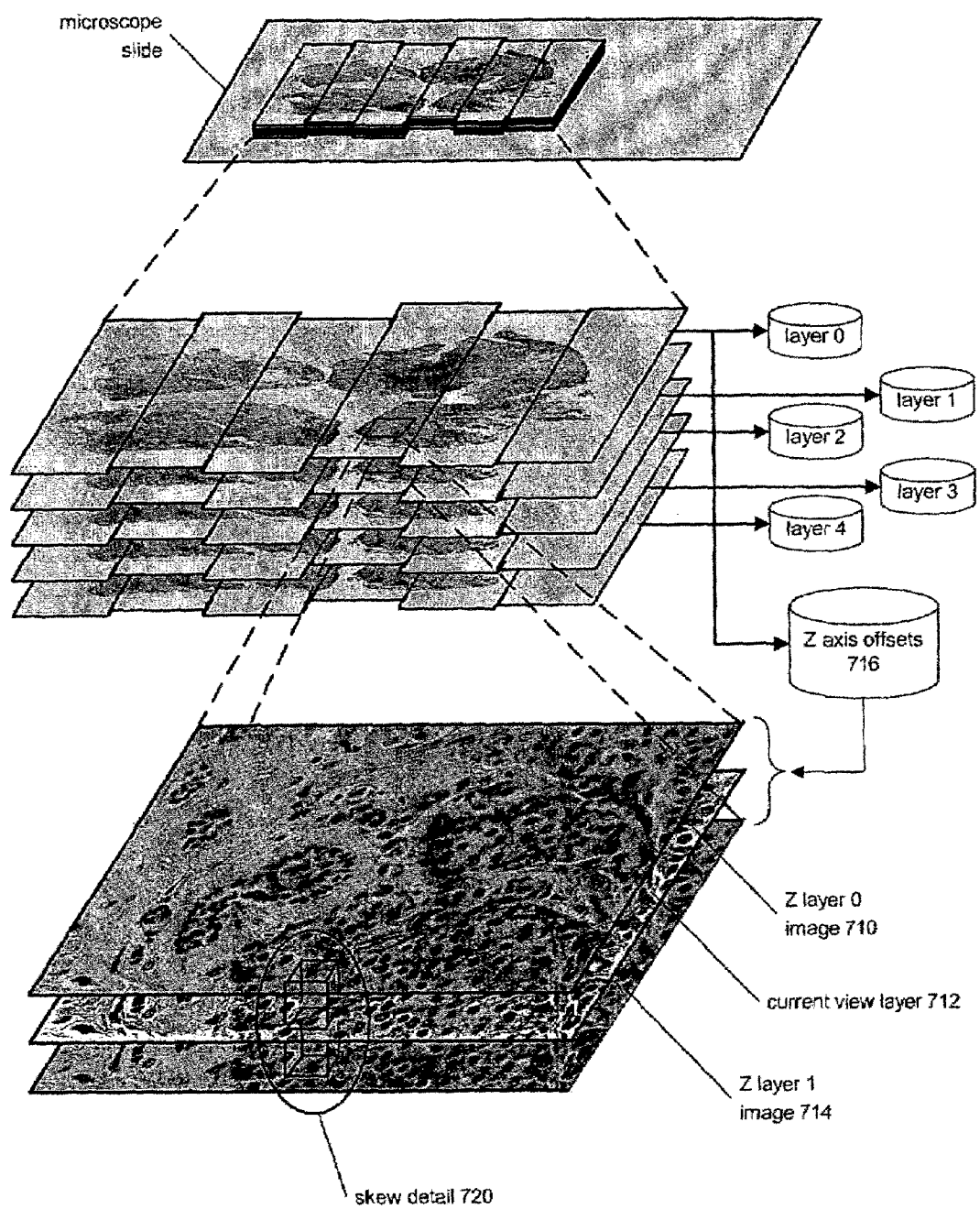
FIG. 8A is a block diagram illustrating an example three dimensional virtual slide according to an embodiment of the present invention.

FIG. 8A is a block diagram illustrating an example three dimensional virtual slide according to an embodiment of the present invention. Three dimensional virtual slides comprise multiple image planes in the vertical dimension. For example, when a tissue specimen on a microscope slide has substantial thickness, it is frequently difficult to capture the entire specimen in a single vertical focal plane. Accordingly, the microscope slide is scanned (i.e., digitized) in several vertical layers at different focal planes, with each vertical layer making a separate virtual slide image.

In the illustrated embodiment, the microscope slide is scanned at five separate vertical layers and a virtual slide is created and stored for each of the five layers (0-4). The vertical axis (also referred to herein as the "Z axis") offset for each layer is also stored to create a composite image file comprising the virtual slides for each layer and the vertical axis offsets 716. Accordingly, when a client viewer requests a view on the Z axis that is between two of the five layers, such as the current view layer 712 which falls between layer 0 image 712 and layer 1 image 714, the immediate upper layer and immediate lower layer are interpolated to provide the user with a view at the requested vertical level.

Figure 8B:
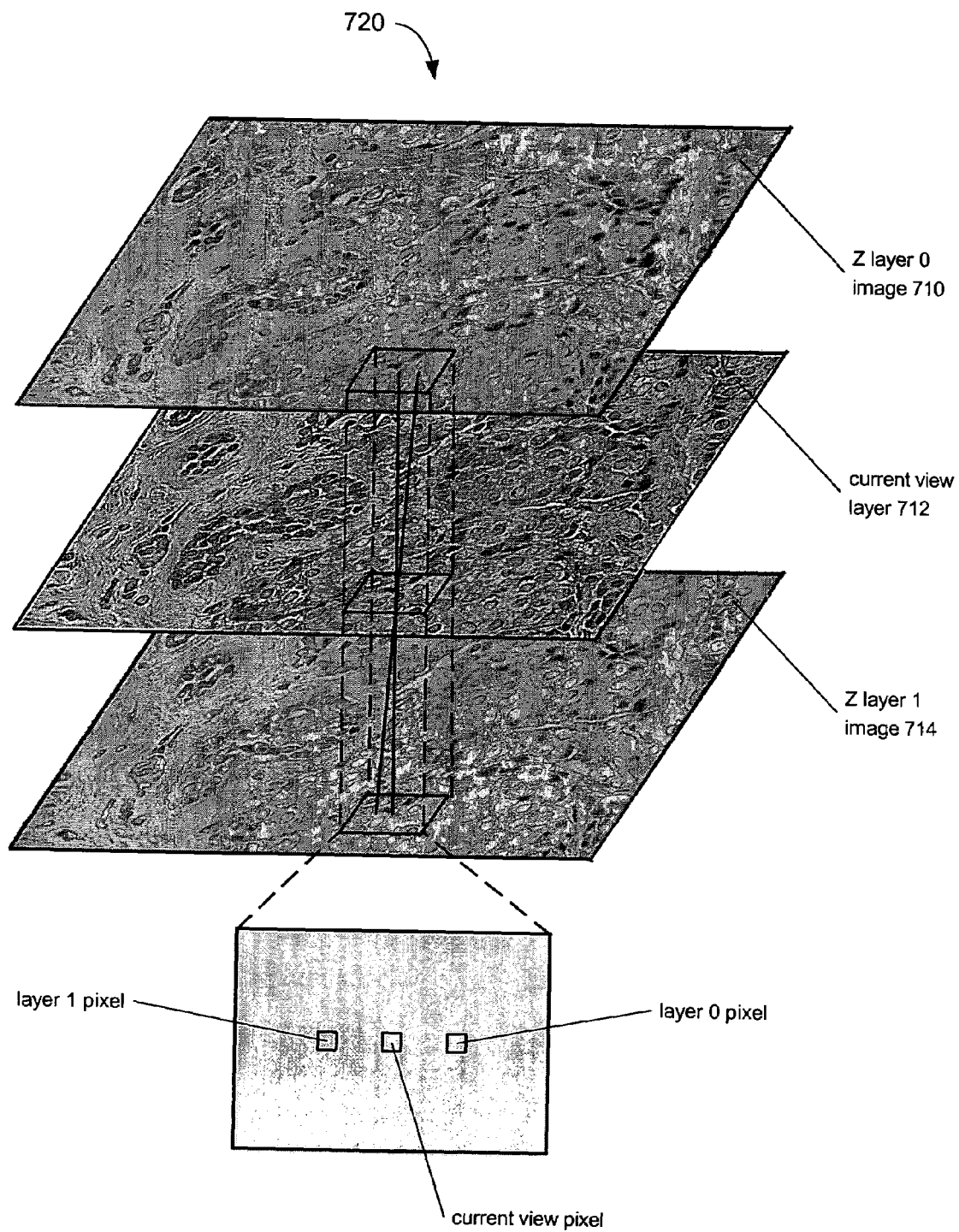
FIG. 8B is a block diagram illustrating an example skewed three dimensional virtual slide according to an embodiment of the present invention.

FIG. 8B is a block diagram illustrating a three dimensional virtual slide skewed 720 according to an embodiment of the present invention. An advantage of interpolating the current view level on the vertical axis is the ability to skew the resulting current view. For example, the image pixels from the layer 0 image 710 can be shifted in one direction and the image pixels from the layer 1 image 714 can be shifted in the opposite direction. Accordingly, the resulting current view level image provides a point of view that approximates an angle to the actual scan direction. By manipulating the skew of a three dimensional virtual slide, a user can advantageously see a rotating three dimensional picture of the subject tissue or cells on the slide.

Figure 8C:
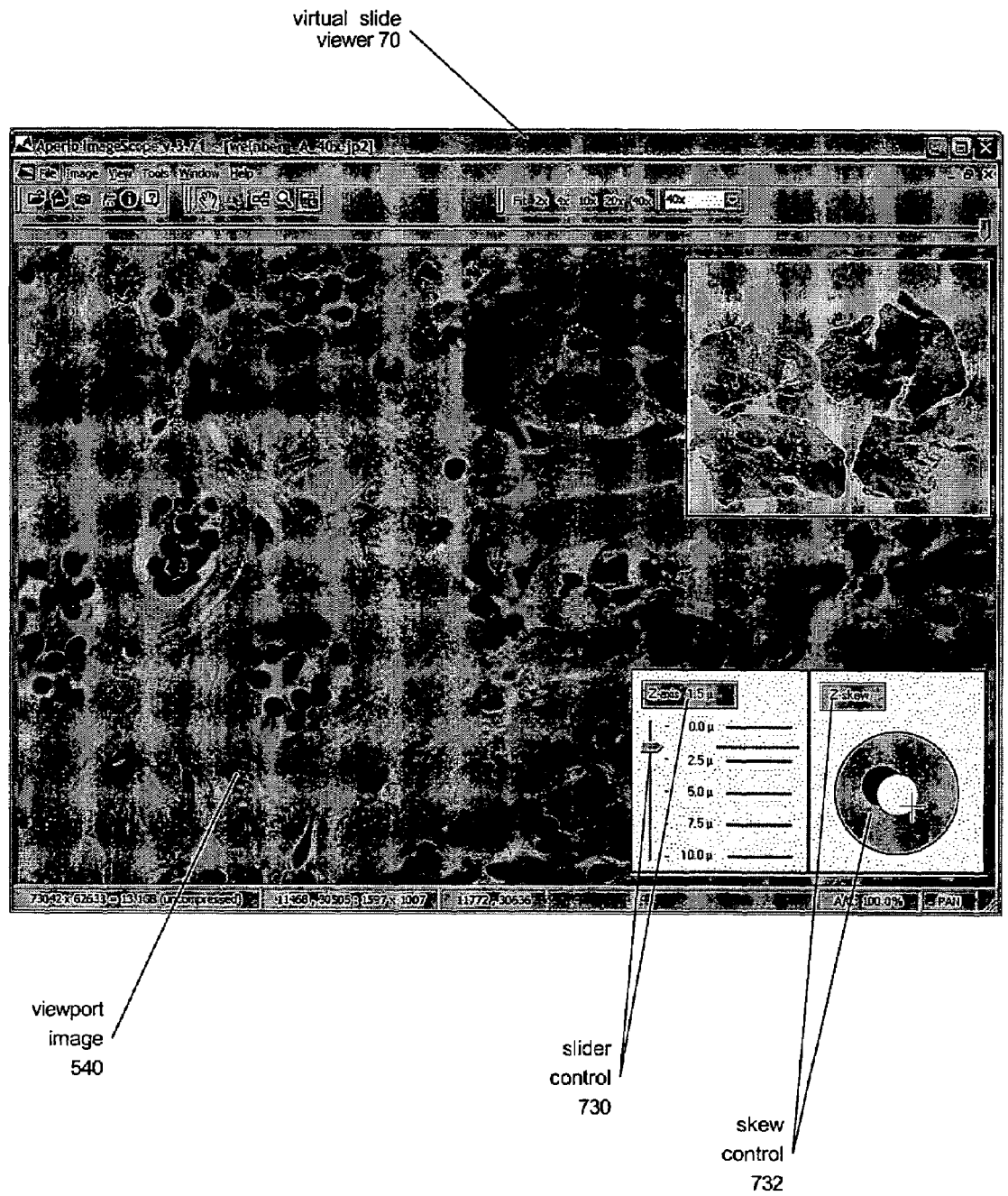
FIG. 8C is a screen shot illustrating an example three dimensional virtual slide viewing window according to an embodiment of the present invention.

FIG. 8C is a screen shot illustrating an example three dimensional virtual slide viewing window according to an embodiment of the present invention, built into a virtual slide viewer 70. In the illustrated embodiment, the viewport image 540 shows the current viewing level that is interpolated from the next higher image layer and the next lower image layer. A slider control 730 for the vertical layer depth is provided to allow the user to change the display in the viewport along the Z axis. Additionally, a skew control 732 is provides to allow the user to dynamically alter the skew direction and amount of skew for the virtual slide image in the viewport. In one embodiment, dragging the crosshair in the skew control window changes the three dimensional point of view. Advantageously, the dark shadow circle shows the relationship of the point of view (e.g., the crosshair) to an object (e.g., the white circle).

Exemplary Embodiment

An example implementation of the present invention will now be described with respect to FIGS. 9A-9F. The exemplary embodiment is described by way of example only and should not be construed to limit the breadth and scope of the invention as set forth in the prior description and claims.

Figure 9A:
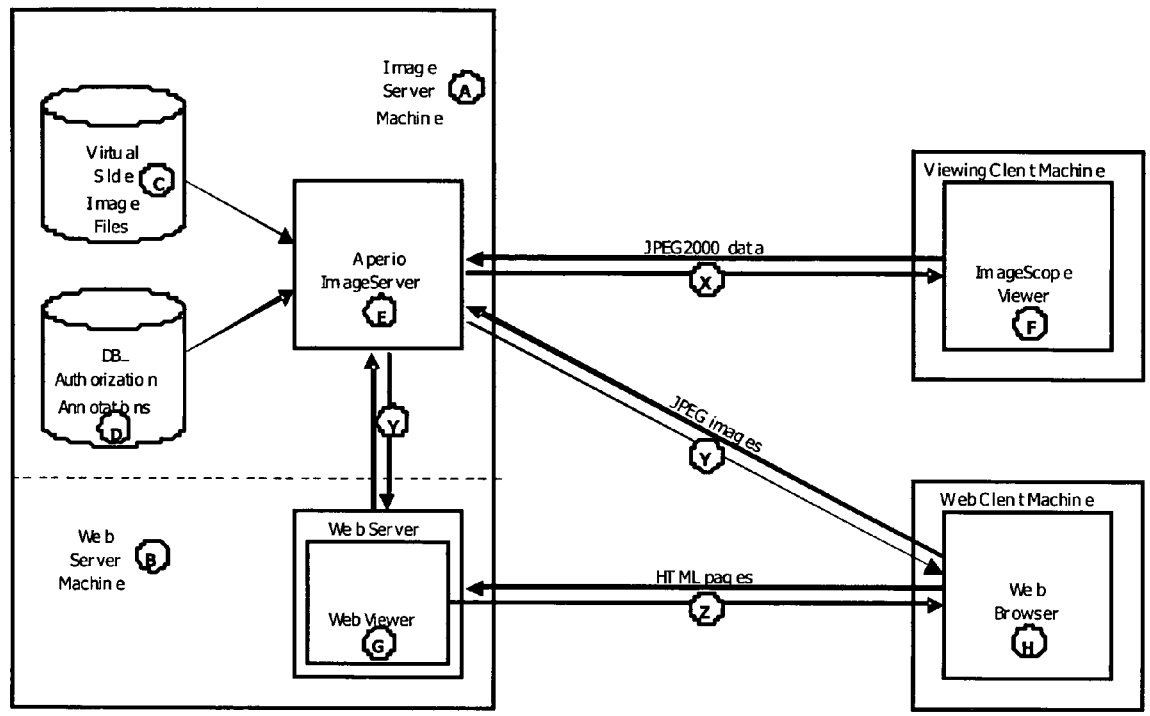
FIGS. 9A-9F are block diagrams illustrating an exemplary embodiment for viewing virtual microscope slide images.

FIGS. 9A-9F are block diagrams illustrating an exemplary embodiment for viewing virtual microscope slide images. FIG. 9A illustrates the components of the virtual slide viewing system and the interfaces between them as described below.

The illustrated embodiment comprises a computer system for viewing and managing digitized scans of microscope slides ("virtual slides"). The computer system has one or more server machines which store virtual slide information, and one or more client machines which are used for viewing slide information. The computers in the system communicate using HTTP requests over TCP/IP (the standard networking protocol used on the Internet). The system's computers may be physically near each other, communicating over a local area network ("LAN"), or physically separated, communicating over a wide area network ("WAN"). A key feature of the system is that it proves excellent performance over WANs; that is, it does not require the inter-machine bandwidth of a LAN.

The server machines are typically powerful PCs featuring Intel architecture processors and running Microsoft Windows or Linux. The system architecture is independent of the details of the server implementation. All the server components of the system may be co-resident on one server machine, or they can be separated to facilitate higher-performance or maintenance considerations.

Two viewing environments are provided by the system. The client viewing interface uses a stand-alone viewing program ("ImageScope") which provides a simple and elegant graphical user interface ("GUI"). The web viewing interface uses any standard Internet browser; no client-side applets, plug-ins, or other software is required. The client viewing interface runs on any Intel-architecture computer and on any version of Microsoft Windows. The features of the system are independent of the client machine configuration. The web viewing interface runs on any computer whatsoever, on any version of any operating system, so long as the environment provides a standard web browser capable of processing HTML pages and displaying JPEG images.

A—ImageServer machine. This computer hosts virtual slide images and provides a network application program interface ("API") used for accessing slide data. This machine is an Intel-architecture computer running Microsoft Windows or Linux, typically a powerful PC equipped with significant memory (for caching) and large amounts of disk storage (for storing virtual slides).

B—Web server machine. This computer hosts a website used for accessing virtual slide data using the web interface. The WebViewer software is integrated with the webserver. This machine may be an Intel-architecture computer running Microsoft Windows and Microsoft Internet Information Server (IIS), or any architecture computer running Apache. It is possible for the Web server machine to be the same as the ImageServer machine.

C—Virtual slide image files. Virtual slides are stored as individual files with a typical size of 200 MB-4 GB. The ImageServer machine is often configured with a Redundant Array of Independent Disks ("RAID") for capacity and robustness.

D—Database. Virtual slide information including authorization data and annotations are stored in an SQL database. The database is typically resident on the ImageServer machine although it need not be. A typical implementation uses Microsoft Database Engine ("MSDE") or Microsoft SQLServer. Access to the database is via a service provided as part of the system. The interface to the service is HTTP over TCP/IP, enabling database access to be distributed.

E—ImageServer. The ImageServer is a stand-alone application which provides a network API for accessing virtual slide data. The ImageServer accesses virtual slide image files and has an interface to the database for authorization and accessing annotation data.

F—ImageScope viewer. ImageScope is a stand-alone application which provides a simple and elegant graphical user interface for viewing slide information. ImageScope interfaces to an ImageServer using its network API, or it can read virtual slide files directly.

G—WebViewer. The WebViewer software runs under a standard web server to deliver an HTML user interface for viewing slide information in a web browser. The HTML pages contain image tags (<IMG>) which cause the web browser to request JPEG image information from the ImageServer. The combination of the HTML pages and the JPEG images form the WebViewer interface.

H—Web browser. Any standard web browser on any platform can be used for viewing virtual slide data using the WebViewer.

X—Image block API. The ImageServer supports an HTTP over TCP/IP message interface for accessing blocks from virtual slide files. These blocks are decompressed and processed by the ImageViewer (client-side).

Y—Image subregion API. The ImageServer supports an HTTP over TCP/IP message interface for accessing subregions from virtual slide files. These regions are decompressed and processed by the ImageServer (server-side) and recompressed as JPEG images, which are transmitted to the browser.

Z—HTML interface to web server. This is a standard HTTP over TCP/IP interface between a web browser and a web server used to deliver HTML pages to the browser. The WebViewer dynamically generates the pages and processes the response data.

Figure 9B:
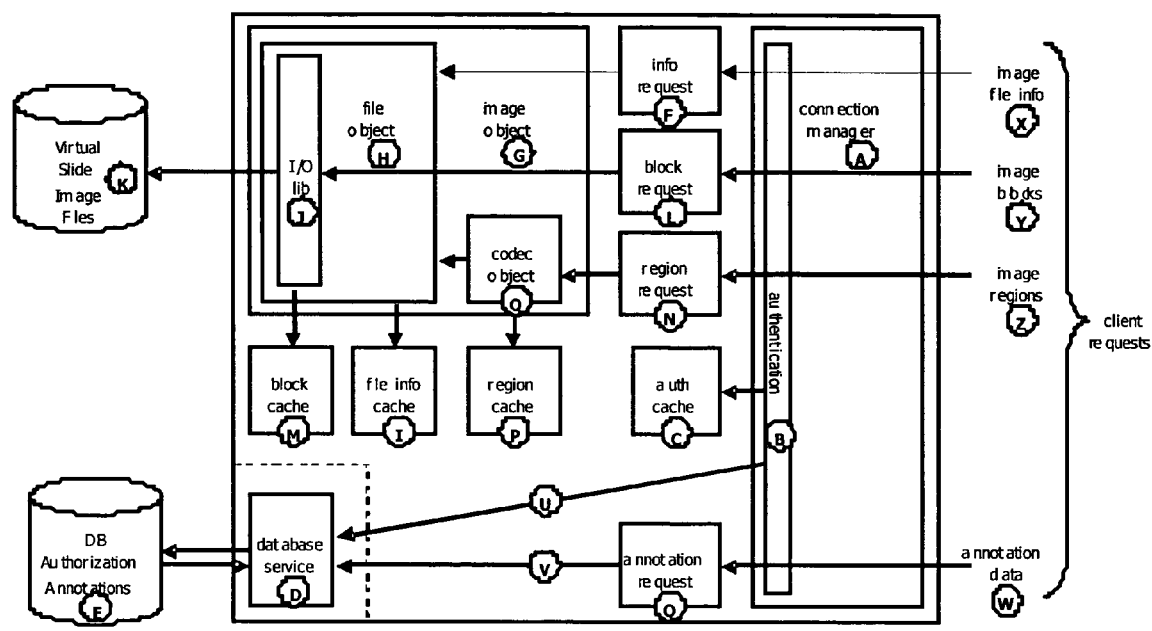

FIG. 9B illustrates the internal implementation details of the image server as described below.

The ImageServer is a stand-alone application which provides a network API for clients to access virtual slide image data. Clients can access image blocks (raw compressed image data) or image regions (image data which have been decompressed, scaled, transformed, filtered, and recompressed into JPEG format). Access is also provided for various image attributes (dimensions, descriptive text, etc.) and annotation information.

The ImageServer can serve multiple clients concurrently, and employs several memory caches to speed access to image data. All requests to the server are stateless. Requests are made via HTTP over TCP/IP. HTTP 1.1 request pipelines are supported (multiple requests can be made sequentially over one socket connection).

The ImageServer includes a connection manager component which accepts new socket connections from clients and manages all client requests. Each client request may optionally include an HTTP Authentication: header. This header is created by web browsers (when a user enters userid/password authentication information) and by stand-alone client programs like ImageScope. The connection manager validates all incoming requests authentication information. Authentication is performed at the directory level. Some directories can be "public" (no authentication is required), while others can require explicit authentication before any images within the directory can be viewed.

A—The connection manager component accepts new socket connections from clients, manages all client requests, and performs authentication checking.

B—Authentication credentials are presented by clients in each request (all connections are stateless), by supplying userid/password information in the HTTP Authentication: header.

C—An authentication cache is maintained by ImageServer to avoid having to access the authentication database on each request. The cache is refreshed periodically as new connections are established, or explicitly when a RESET request is received.

D—A database service provides the interface to the database. The service accepts HTTP requests, enabling the database potentially to be located on a separate machine from ImageServer. The service uses standard SQL requests to access database information.

E—A SQL database is used to store authentication and annotation information. This database is typically implemented using Microsoft Database Engine ("MSDE") but can also be SQLServer or any other SQL-compliant database.

F—Image information requests are made by clients to return attributes such as image dimensions, descriptive text, and pyramid structure. Info requests use properties of an Image Object to return data.

G—An Image Object is instantiated for each separate virtual slide image managed by the ImageServer, and provides properties and methods for interfacing to a virtual slide. A cache of recently accessed objects is maintained for performance purposes. Image Objects are used throughout the system to isolate applications from the detailed implementation of virtual slides.

H—A File Object is instantiated within an Image Object for encapsulating access to a virtual slide file, and provides properties and methods for interfacing to such files.

I—A file information cache is maintained across all File Objects for performance purposes. This enables Image Objects to be instantiated and destroyed as requests are made without having to reload all information for recently accessed files. The file information cache is refreshed periodically as File Objects are instantiated, or explicitly when a RESET request is received.

J—An I/O library is used by File Objects to access virtual slide file information. This library encapsulates the details of the Tagged Image File Format ("TIFF") file headers.

K—Virtual Slide image files are stored on the ImageServer machine as ordinary files (albeit very large ones).

L—Block requests are made by clients which are capable of decoding image file blocks directly (that is, clients which include the Image Object). This includes the ScanScope viewer as well as the Algorithm Framework. Block requests are passed through the image object directly to the File Object and then passed to the I/O library. Block requests are fast, because very little processing is required on the server, and dense, because the original JPEG2000 compression of the virtual slide images is preserved across the client/server interface.

M—A block cache is maintained across all File Objects for performance purposes, on a most recently used ("MRU") basis. The size of the block cache is a function of the amount of memory configured on the ImageServer machine and by parameters passed to the ImageServer process.

N—Region requests are made by clients which are not capable of decoding image file blocks directly (such as web browsers). Note "region" refers to any arbitrary sub-region of an image; this is not a fixed property of the image files or the way they were acquired. In this the example embodiment being described differs fundamentally from other systems where image data are acquired as tiles and stored as tiles, and the tiles are a physical property of the images. Subregions of an image can be requested at any (X,Y) location within the image, at any resolution, and of any dimensions. Regions are returned encoded as JPEG images for compatibility with clients which cannot interpret JPEG2000 data. Region requests are slower than block requests because of the amount of preprocessing required on the server, and are less dense than block requests because image data are returned encoded as JPEG rather than JPEG2000.

0—A Codec Object is instantiated with an Image Object to encapsulate different compression mechanisms. Typically JPEG2000 is preferred for virtual slide images because of its high image fidelity, but JPEG and LZW are also supported, as well as raw images (no compression).

P—A region cache is maintained across all Image Objects for performance purposes, on a most recently used basis. The size of the region cache is a function of the amount of memory configured on the ImageServer machine and by the parameters passed to the ImageServer process.

Q—Annotation requests are made by clients to request and update annotation information for images. Annotations are stored in XML and passed as a "blob" directly from the database back to clients, via requests made to the database service. Clients may update annotation information for images if they have proper authentication.

W—Annotation data interface. Clients make HTTP requests and receive XML-formatted image annotation data in response. Annotation data also may be updated with an HTTP post containing XML-formatted image annotation data.

X—Image file information interface. Clients make HTTP requests and receive XML-formatted response data to obtain image attributes.

Y—Image block interface. Clients make HTTP requests and receive image file blocks in response. Blocks are requests by (X,Y) location and level. Clients are responsible for decompressing image file blocks (using a JPEG2000 codec) and scaling to appropriate resolution.

Z—Image region interface. Clients make HTTP requests and receive JPEG images in response. Regions are arbitrary subregions of images, and are requested by (X,Y) location and resolution, and by desired dimension. Decompression of JPEG2000 and scaling to appropriate resolution are done by the ImageServer process.

Figure 9C:
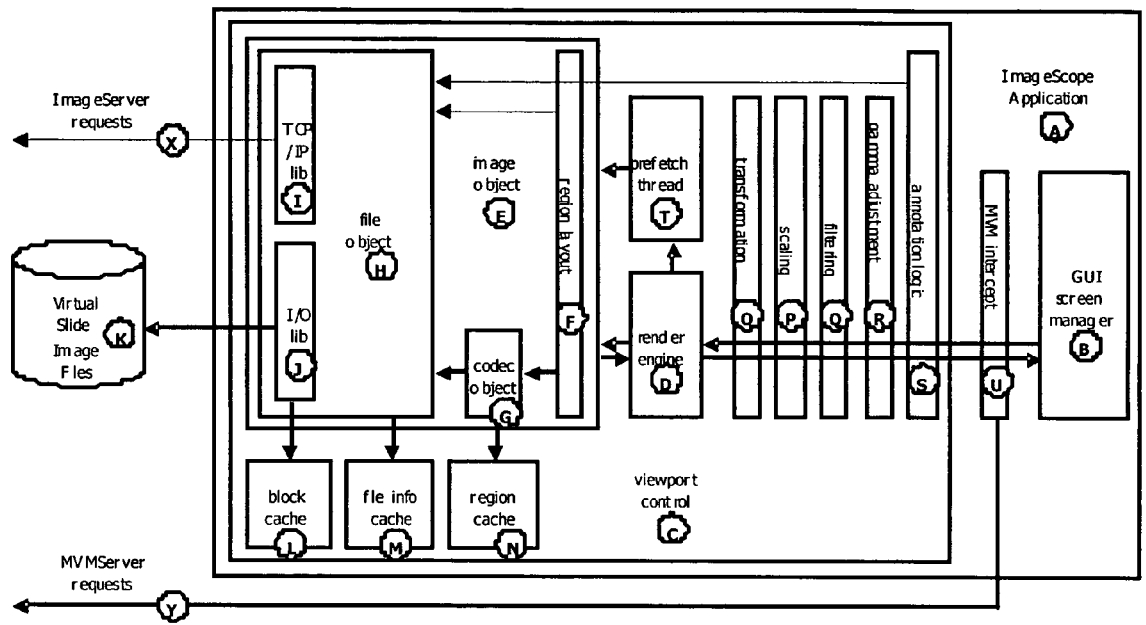

FIG. 9C illustrates the internal implementation details of the image scope viewer as described below.

The ImageScope is a stand-alone application which provides a simple and elegant graphical user interface for viewing slide information. ImageScope interfaces to an ImageServer using its network API, or it can read virtual slide files directly.

ImageScope provides unique features to facilitate examination of virtual slides, including: realtime panning and zooming of very large virtual slides, support for multiple concurrent images, and synchronized windows, JPEG2000 (wavelet) image quality, predictive data prefetching to improve performance, block and region caching to improve performance, realtime adjustable gamma (RGB color mapping), realtime application of convolution filters, realtime orthogonal transformations (90° rotations and mirroring), support for displaying and authoring annotations in layers, support for virtual microscopy conferencing ("VMC"), and 3D viewing of slide data which have been acquired in multiple Z-axis scans.

ImageScope is implemented with a novel architecture which encapsulates most of its functionality in an ActiveX control called the viewport. The viewport control can be easily incorporated in a variety of applications to provide virtual slide viewing capability.

The viewport control employs extensive caching and prefetching techniques to optimize performance. Applications can instantiate multiple viewports which share inter-object caches, for maximum performance and utilization of available memory. The viewport itself encapsulates an Image Object which in turn encapsulates a File Object; the Image Object and File Object are shared with the ImageServer program.

A key attribute of the ImageScope program and viewport control is the ability to view very large virtual slide images over a wide-area network, with relatively slow (300K) network bandwidth. For this reason, screen refreshes are never synchronous, instead the viewport displays the best version of an image view currently available from its cache, and continuously attempts to fetch higher and higher resolutions versions of this view from the ImageServer, updating the screen as it does so. The effect for an end-user is a feeling of responsiveness and independence from the bandwidth of their connection.

A—The ImageScope application, which hosts the graphical user interface ("GUI") for accessing virtual slides, and acts as a container for multiple instances of the viewport ActiveX control.

B—The GUI screen manager encapsulates the main logic of the ImageScope program, managing the virtual slide windows and all keyboard and mouse input.

C—The viewport ActiveX control. The properties and methods of this control fully encapsulate all access to a virtual slide. The control window is the surface of the windows which display slide information.

D—A "render engine" is the heart of the viewport control. This engine uses cached data to build the "best" version of any view of a virtual slide image, at any location, dimensions, and resolution. As "better" versions are available (more data are retrieved from the ImageServer) the engine updates the currently displayed screen.

E—An Image Object is instantiated by the viewport control to encapsulate the virtual slide image, and provides properties and methods for interfacing to a virtual slide.

F—The Image Object includes logic for region layout, rendering any region of the virtual slide at any desired level of resolution. The logic can be synchronous (request required image information), as when invoked by the prefetch thread, or asynchronous (use only available image information), as when invoked by the render engine.

G—A Codec Object is instantiated with an Image Object to encapsulate different compression mechanisms. Typically JPEG2000 is preferred for virtual slide images because of its high image fidelity, but JPEG and LZW are also supported, as well as "raw" images (no compression).

H—A File Object is instantiated within an Image Object for encapsulating access to a virtual slide file, and provides properties and methods for interfacing to such files. The File Object allows location independent access to virtual slide files, which can be either remote (accessed from an ImageServer via the TCP/IP library) or local (accessed from a local filesystem via the I/O library).

I—A TCP/IP library is used by File Objects to encapsulate the network interface to an ImageServer. This library uses the block interface to the server.

J—An I/O library is used by File Objects to access local virtual slide files. This library encapsulates the details of the TIFF file headers (Tagged Image File Format).

K—Virtual Slide image files may be stored locally and accessed using the viewport (and viewed using ImageScope).

L—A block cache is maintained across all File Objects for performance purposes, on a most recently used (MRU) basis. (This cache spans multiple viewports within one program.) The size of the block cache is a function of the amount of memory configured on the ImageScope machine and by parameters passed to the ImageScope program.

M—A file information cache is maintained across all File Objects for performance purposes. (This cache spans multiple viewports within one program.)

N—A region cache is maintained across all Image Objects for performance purposes, on a most recently used (MRU) basis. (This cache spans multiple viewports within one program.) The size of the region cache is a function of the amount of memory configured on the ImageScope machine and by the parameters passed to the ImageScope program.

O—The viewport supports realtime orthogonal transformations ($90°$ rotations and mirror flips). These transformations are applied in the render engine.

P—The viewport supports realtime scaling to any desired resolution. This capability builds on the Virtual Slide image levels. Scaling is built into the render engine.

Q—The viewport supports realtime filtering, predefined or custom 5×5 convolution kernels can be applied to the image. Filtering is built into the render engine.

R—The viewport supports realtime gamma adjustment, enabling the color mapping of RGB values to actually displayed pixels to be adjusted. This capability is vital for compensating for difference in ambient lighting and monitor characteristics when virtual slides are viewed. Gamma adjustment is built into the render engine.

S—The viewport supports display and authoring of annotation layers. Annotation display is built into the render engine.

T—The viewport incorporates a prefetch thread which dynamically fetches image data for displayed virtual slides in anticipation of render engine requests. The prefetch logic determines a "motion" for current user interaction with an image, and uses this to guide prefetching (e.g. if a user is scrolling an image to the right, new image data further to the right are prefetched).

U—ImageScope contains a VMC Intercept which sits between the GUI Screen Manager and the viewport control. The VMC Intercept relays user commands to the viewport back to a VMCServer, and also accepts commands from a VMCServer and feeds them into the viewport as if they came from the GUI Screen Manager.

X—ImageServer interface. The viewport/File Object/TCP/IP library makes HTTP requests to an ImageServer and receives virtual file blocks in return. This interface is also used for retrieving image attributes.

Y—VMCServer interface. The MVC intercept makes HTTP requests to a VMCServer and receives XML-formatted responses. This interface is used for passing intercepted commands to the VMCServer (when this application is "leading" the session) and for receiving commands from the VMCServer (when this application is "following").

Figure 9D:
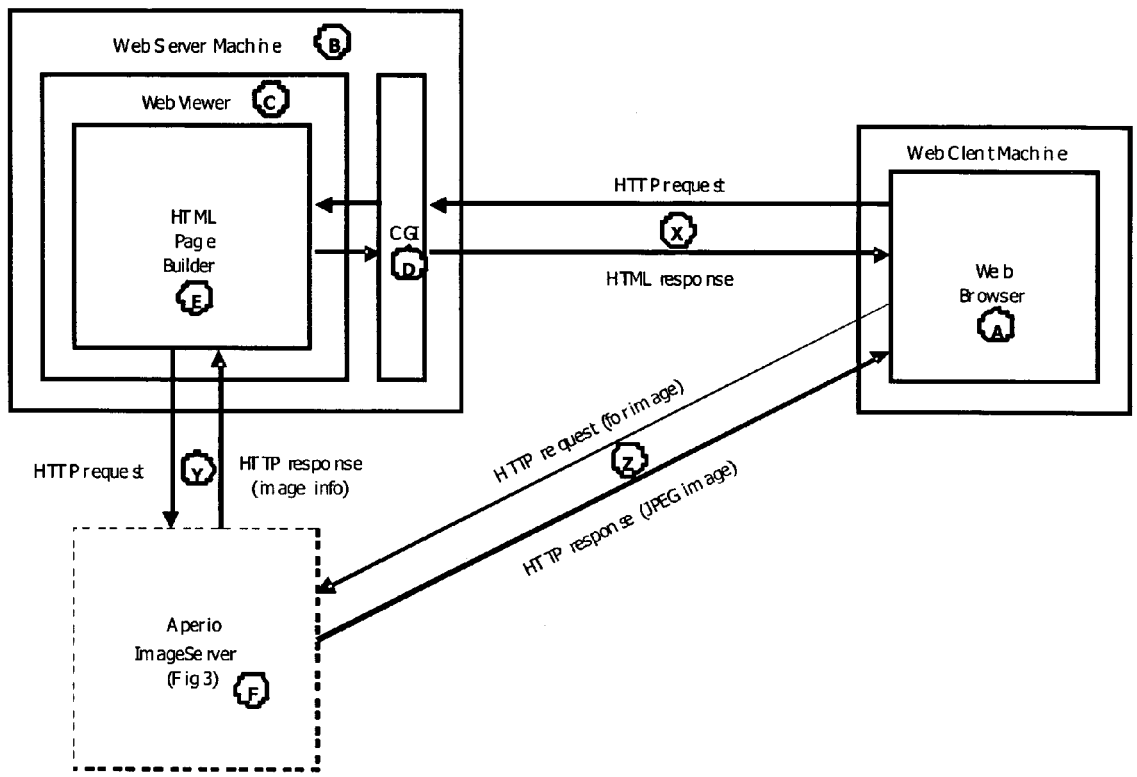

FIG. 9D illustrates the components of the WebViewer and the interfaces between them as described below.

The WebViewer software runs under a standard web server to deliver an HTML user interface for viewing slide information in a web browser. The HTML pages contain image tags (<IMG>) which cause the web browser to request JPEG image information from the ImageServer. The combination of the HTML pages and the JPEG images form the WebViewer interface A key feature of the WebViewer interface is that it is available in any standard web browser, without any additional applets, plug-ins, or other software. This makes it highly portable (available on virtually any platform) and enables new users to view virtual slide data instantly.

A—A web browser. Any standard browser on any platform is supported.

B—The web server machine. This is typically either Microsoft Internet Information Server (IIS) running under Windows, or Apache running under Linux or Unix. Any web server which supports a CGI interface on a platform which supports Korn Shell scripts is supported.

C—The WebViewer scripts. These run under the web server process and are invoked through the Common Gateway Interface (CGI). The scripts require a resident Korn Shell interpreter. The WebViewer builds HTML pages which comprise the interface for web viewing, and processes input (mouse clicks) from the interface.

D—CGI is the Common Gateway Interface, a standard mechanism provided by web servers for running programs in a web environment which process HTTP input and generate HTML page content as output.

E—The WebViewer contains an HTML Page Builder module which generates the HTML used for displaying virtual slides. Each slide region is built up from numerous smaller regions to enable the web browser to fetch multiple image subregions in parallel, and to enable caching of image subregions.

F—An ImageServer process provides the actual image data. Image attributes are requested by the HTML Page Builder. The HTML pages contain arrays of IMG tags which contain URLs that request image data from the ImageServer. These URLs use the region interface to the ImageServer to request JPEG subregions, which are then displayed by the web browser.

X—The HTTP interface between the web browser and web server is standard; HTTP requests are sent by the browser, routed to the WebViewer through the CGI, and HTML pages are generated and returned to the browser.

Y—The WebViewer makes HTTP requests of the ImageServer directly to obtain image attributes.

Z—The web browser makes HTTP requests of the ImageServer from IMG tags generated in the HTML pages; these requests use the region interface to the ImageServer and JPEG images are returned in response.

Figure 9E:
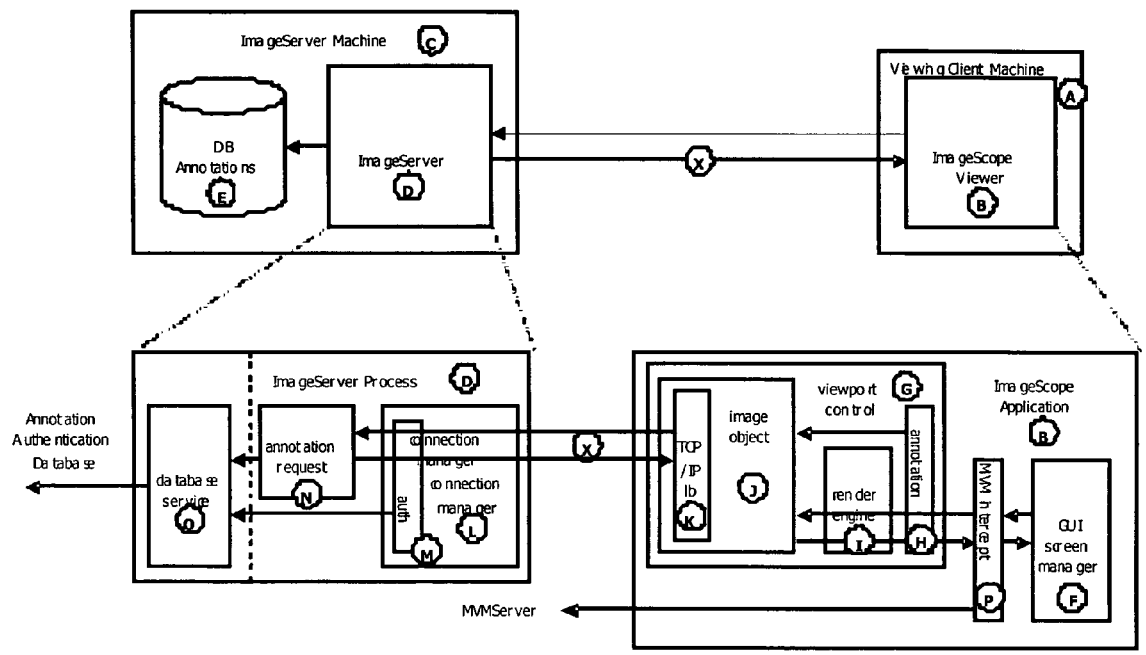

FIG. 9E illustrates the detailed implementation of annotation support in the Virtual Slide viewing system as described below.

The Virtual Slide viewing system supports multiple annotations on multiple layers per image. Annotations are composed of annotation regions, which take one of four forms: (i) a rectangular region; (ii) an elliptical region; (iii) an arrow designating a particular spot; and (iv) an arbitrary polygonal region with an arbitrary number of vertices.

Regions are always located relative to the baseline image of a virtual slide, and are independent of resolution (that is, annotation regions scale with the image). Each annotation region can have one or more attributes associated with it of the form "key=value". The set of "keys" is the same for all regions within an annotation.

All the regions in an annotation together form an annotation layer. Annotation layers can be thought of as a plastic overlay on an image. Each layer can be independently displayed or hidden. Layers can have one or more attributes associated with them of the form "key=value". The "keys" for annotation layers may differ from the "keys" for any one layer's regions.

The viewport control provides properties and methods for managing the display of image annotations. As image data are formatted for display, enabled annotation layers are drawn over the image.

The ImageScope application provides a set of GUI tools for authoring annotations. Using these tools, the user can interactively "draw" annotation regions over the virtual slide on the surface of a viewport control. A floating window provides an interface for entering attributes associates with annotation regions and layers.

All annotations for an image are stored as an XML string. The viewport control formats the XML string, which may be saved to disk in a local file, or transmitted to the ImageServer for storage in the database. Annotations may similarly be retrieved from the database or a local file.

A—Viewing client machine. The computer on which ImageScope is run.

B—ImageScope viewer. The application that provides the user interface for displaying and authoring annotations.

C—ImageServer machine. The computer on which ImageServer is run.

D—ImageServer application. The process which provides a network API for accessing virtual slide image data, including annotations.

E—Database. This SQL database (typically MSDE or SQLServer) stores annotation information on the server.

F—The GUI Screen Manager component of ImageScope manages the input tools and mouse movements used to author annotations.

G—The viewport control encapsulates all access to a virtual slide, including the annotation display logic. Access to annotations is provided via an open API.

H—The annotation logic inside the viewport renders all annotations for the virtual slide over the image data, as required.

I—The render engine of the viewport control builds image regions for display which are passed to the annotation display logic.

J—An image object is instantiated inside each viewport control to encapsulate access to the virtual slide file itself.

K—The TCP/IP library is used by an image object to perform request/response communication back to the ImageServer.

L—The connection manager of the ImageServer accepts new socket connections and manages all requests from clients.

M—An authentication layer inside the connection manager validates the authentication credentials of each request, including requests for annotations. Authentication information is maintained separately for each annotation layer for an image; some users may have read-only access to some layers, and update access to others.

N—Annotation requests are passed to a database service using an HTTP interface.

O—A database service provides the interface between ImageServer and the database, enabling the database potentially to be located on a separate machine.

P—The VMC Intercept in ImageScope routes all commands to the viewport control back to the VMCServer (if the user is the session "leader"), and/or routes commands from the VMCServer to the viewport (if the user is a session "follower"). This includes commands for annotation display and authoring.

Figure 9F:
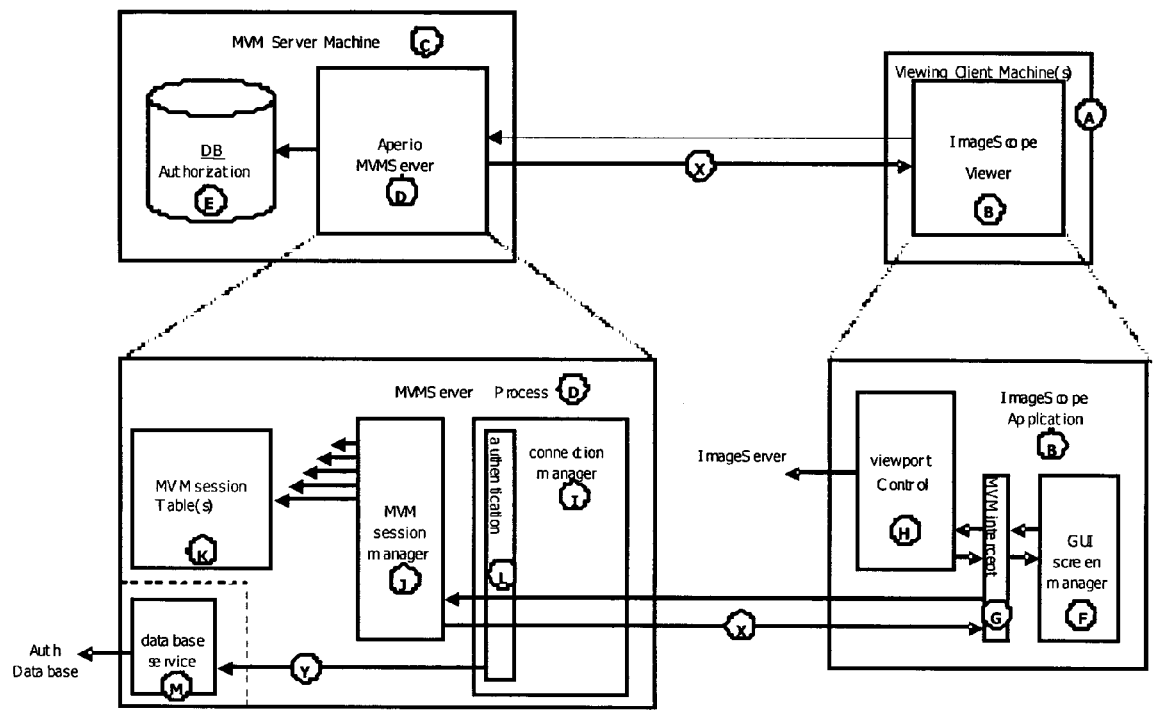

FIG. 9F illustrates the internal implementation details of VMC support within the Virtual Slide viewing system as described below.

VMC is a technique wherein multiple users concurrently participate in a viewing session, viewing the same virtual slide. Each user's view is synchronized to the others, so everyone sees the same information.

At each moment one user in each session is the session "leader", the other users are "followers". The leader pans and zooms, changes views, draws annotations, etc., and each of these commands is relayed to all the followers. The leader may pass session leadership to any other user at any time. Followers may signal the leader that they would like to lead the session. The VMC server maintains a queue of followers waiting to lead for each session (in FIFO order). When the leader passes session leadership to another user, s/he may explicitly designate a particular user or pass leadership to the first waiting follower.

VMC sessions are established using an VMC server machine. The first user to connect to the VMC server creates the session, gives it a descriptive name, and assigns a password. Subsequent users who connect to the VMC server can identify the session by its descriptive name and may sign on by supplying the password. There is no limit to the number of users which may concurrently join an VMC session. The first user who defines a new session becomes the first leader.

If desired authentication to connect to a particular VMC server may be required. This authentication is to access the server at all, individual sessions then have their own passwords, as established by the first user to connect.

When a new user joins an ongoing VMC session, any images presently open for the session will be opened for the new user, and all windows will be synchronized to the present locations within the session.

During a session the leader may open one or more virtual slides. These slides must be on an ImageServer which is accessible to all users in the session. When the image is opened, all other users in the session simultaneously open the image as well. The ImageServer may be the same machine as the VMC server, although it need not be the same machine nor located in the same place.

When a session leader closes an image, the image is closed for all users in the session.

The session leader may pan and zoom to any location at any magnification in any of the images which are part of the session. All other users follow suit automatically. The size and organization of viewing windows remains under each users control, to allow for the fact that different users may have different sized monitors, etc. Positioning of each image is always relative to the center of the viewing window.

The users in a session may have different bandwidth connections to the ImageServer, and consequently may experience different response times during panning and zooming. The asynchronous nature of viewport updating ensures that no user will be "blocked" during these operations; at worst a user may not see an image view at the same resolution as other users (until the higher resolution data have been retrieved from the server).

The Gamma Adjustment facility of the ImageScope viewer is not synchronized across all users in a session. This remains something each user may adjust to their own liking. This is because the gamma adjustments are typically made to compensate for room lighting and monitor temperature, as well as individual taste, and hence it does not make sense to pass the leader's gamma settings along to all the followers.

The session leader may enable and disable annotations for a virtual slide which was opened as part of an VMC session. All users have the annotations enabled and disabled simultaneously. The session leader may also author new annotation layers and regions. Each user in the session sees the partially completed layers and regions. This is accomplished by relaying the leader's annotation commands to all users, not by synchronization through the annotation database on the ImageServer, because the annotation may be temporary in nature.

In some sessions all users may collaborate on one annotation layer (by passing leadership to one another), in other sessions each user may have their own annotation layer. This is up to the users in a session to decide.

Users may leave an VMC session at any time. All image windows which were part of the session are closed when a user leaves. If the user was the session leader, the "next" follower in the queue becomes session leader. If no followers were waiting to become leaders, a leader is chosen at random. (At any moment, one user must be the session leader.)

The last user to leave an VMC session causes the session to be terminated. The server does not retain any information for terminated sessions.

A—Viewing client machine(s). The computers on which each user is running the ImageScope viewer.

B—ImageScope viewer. The application program which implements the client interface for VMC sessions.

C—VMC Server Machine. The computer on which the VMCServer application is run. This computer may be but need not be the same as the ImageServer machine which provides the images viewed during an VMC session.

D—VMC Server Process. The application which manages VMC sessions by interconnecting the ImageScope viewers together. Clients communicate with the VMC server using HTTP requests over TCP/IP.

E—Database. A SQL database (typically MSDE or SQLServer) stores authentication information. Note this is authentication information for accessing the VMC server, which may differ from authentication information required for accessing images on ImageServer machines.

F—The GUI Screen Manager of ImageScope provides the interface for each user to manage their session. While a user is a session "follower" they cannot pan or zoom or author annotations for any image which is open in the session.

G—The VMC Intercept sits between the GUI Screen Manager and the viewport control(s), and routes all commands given by the session leader to the VMC server. All commands given by session followers are ignored. The VMC Intercept also receives commands from the VMC server for session followers and routes them into the viewport control(s) as if they came from the GUI Screen Manager.

H—The viewport control encapsulates all access to a virtual slide. The properties and methods of this control are the interface between the GUI and the virtual slide (and between the VMC session and the virtual slide). Note that each viewport control makes a connection to an ImageServer for each image in the VMC session, and that these connections are separate from the connections to the VMC server.

I—The Connection Manager in the VMCServer program handles all socket connections and processes all client requests. A persistent socket connection is maintained to each active client in each VMC session (unlike normal HTTP 1.1 requests, these connections are not timed out). This enables commands from a session leader to be sent back to the VMC Intercept in each follower asynchronously.

J—The VMC Session Manager controls the flow of commands in each VMC session (each VMCServer process may be managing multiple VMC sessions concurrently).

K—The VMC Session Tables store information for each active VMC session and all users in each session, including who is the current leader, the current state of all image windows, the queue of followers who wish to be leader, etc.

L—An authentication layer in the Connection Manager validates authentication credentials for each new user which connects to the VMC server. This authentication enables access to the server; the user must then provide the correct password to join an existing session.

M—A database service provides the interface between VMCServer and the database, enabling the database potentially to be located on a separate machine.

X—The interface between the ImageScope client (VMC Intercept) and VMCServer program is HTTP over TCP/IP. Each client has a permanent socket connection to the server during the VMC session. When a client is a session leader, it sends requests to the server and receives responses. When a client is a session follower, it receives requests from the server and sends responses.

Figure 10:
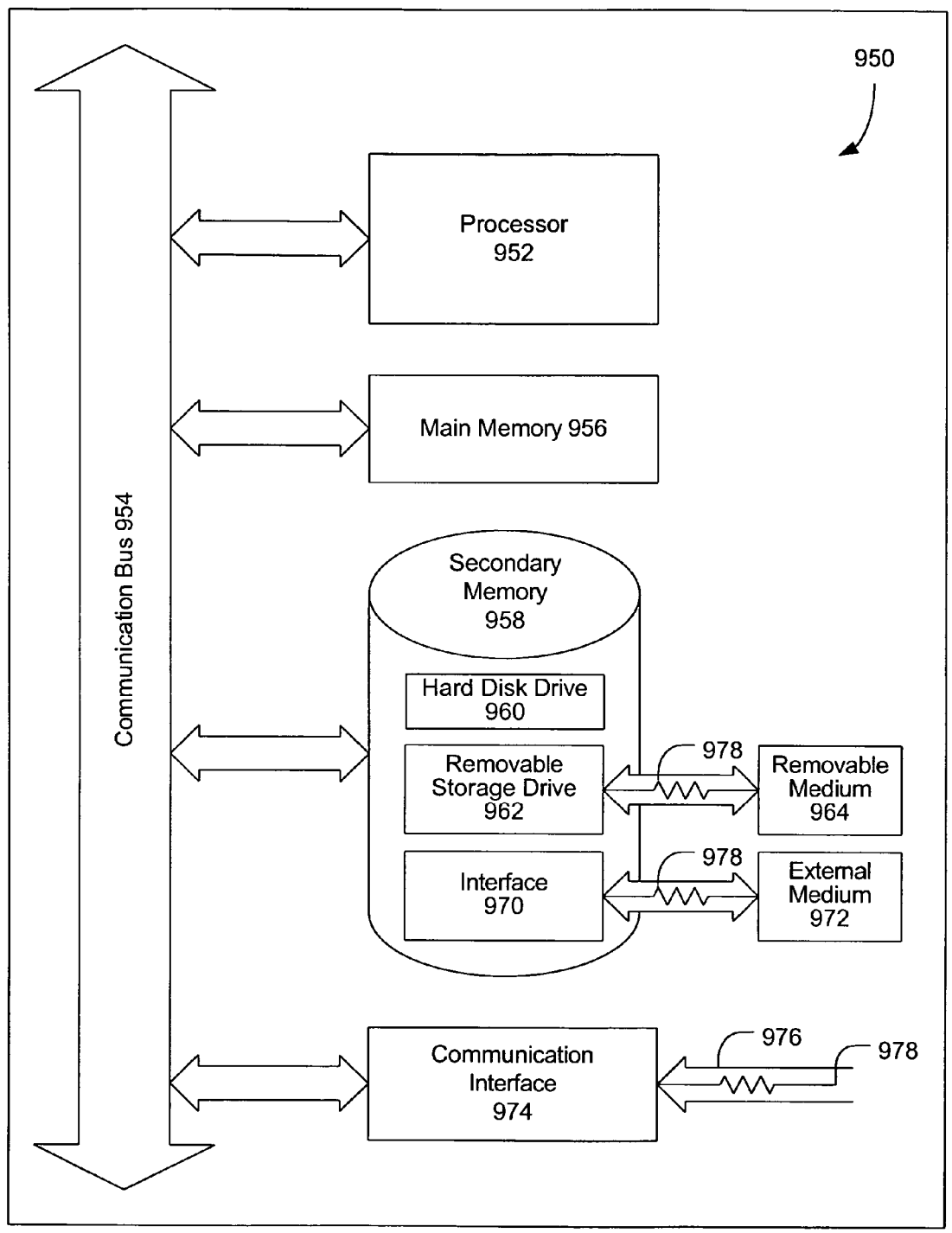
FIG. 10 is a block diagram illustrating an exemplary computer system as may be used in connection with various embodiments described herein.

FIG. 10 is a block diagram illustrating an exemplary computer system 950 that may be used in connection with the various embodiments described herein. For example, the computer system 950 may be used in conjunction with a virtual slide server, a web server, or a viewing client as previously described. However, other computer systems and/or architectures may be used, as will be clear to those skilled in the art.

The computer system 950 preferably includes one or more processors, such as processor 952. Additional processors may be provided, such as an auxiliary processor to manage input/output, an auxiliary processor to perform floating point mathematical operations, a special-purpose microprocessor having an architecture suitable for fast execution of signal processing algorithms (e.g., digital signal processor), a slave processor subordinate to the main processing system (e.g., back-end processor), an additional microprocessor or controller for dual or multiple processor systems, or a coprocessor. Such auxiliary processors may be discrete processors or may be integrated with the processor 952.

The processor 952 is preferably connected to a communication bus 954. The communication bus 954 may include a data channel for facilitating information transfer between storage and other peripheral components of the computer system 950. The communication bus 954 further may provide a set of signals used for communication with the processor 952, including a data bus, address bus, and control bus (not shown). The communication bus 954 may comprise any standard or non-standard bus architecture such as, for example, bus architectures compliant with industry standard architecture ("ISA"), extended industry standard architecture ("EISA"), Micro Channel Architecture ("MCA"), peripheral component interconnect ("PCI") local bus, or standards promulgated by the Institute of Electrical and Electronics Engineers ("IEEE") including IEEE 488 general-purpose interface bus ("GPIB"), IEEE 696/S-100, and the like.

Computer system 950 preferably includes a main memory 996 and may also include a secondary memory 958. The main memory 996 provides storage of instructions and data for programs executing on the processor 952. The main memory 996 is typically semiconductor-based memory such as dynamic random access memory ("DRAM") and/or static random access memory ("SRAM"). Other semiconductor-based memory types include, for example, synchronous dynamic random access memory ("SDRAM"), Rambus dynamic random access memory ("RDRAM"), ferroelectric random access memory ("FRAM"), and the like, including read only memory ("ROM").

The secondary memory 958 may optionally include a hard disk drive 960 and/or a removable storage drive 962, for example a floppy disk drive, a magnetic tape drive, a compact disc ("CD") drive, a digital versatile disc ("DVD") drive, etc. The removable storage drive 962 reads from and/or writes to a removable storage medium 964 in a well-known manner. Removable storage medium 964 may be, for example, a floppy disk, magnetic tape, CD, DVD, etc.

The removable storage medium 964 is preferably a computer readable medium having stored thereon computer executable code (i.e., software) and/or data. The computer software or data stored on the removable storage medium 964 is read into the computer system 950 as electrical communication signals 978.

In alternative embodiments, secondary memory 958 may include other similar means for allowing computer programs or other data or instructions to be loaded into the computer system 950. Such means may include, for example, an external storage medium 972 and an interface 970. Examples of external storage medium 972 may include an external hard disk drive or an external optical drive, or and external magneto-optical drive.

Other examples of secondary memory 958 may include semiconductor-based memory such as programmable read-only memory ("PROM"), erasable programmable read-only memory ("EPROM"), electrically erasable read-only memory ("EEPROM"), or flash memory (block oriented memory similar to EEPROM). Also included are any other removable storage units 972 and interfaces 970, which allow software and data to be transferred from the removable storage unit 972 to the computer system 950.

Computer system 950 may also include a communication interface 974. The communication interface 974 allows software and data to be transferred between computer system 950 and external devices (e.g. printers), networks, or information sources. For example, computer software or executable code may be transferred to computer system 950 from a network server via communication interface 974. Examples of communication interface 974 include a modem, a network interface card ("NIC"), a communications port, a PCMCIA slot and card, an infrared interface, and an IEEE 1394 fire-wire, just to name a few.

Communication interface 974 preferably implements industry promulgated protocol standards, such as Ethernet IEEE 802 standards, Fiber Channel, digital subscriber line ("DSL"), asynchronous digital subscriber line ("ADSL"), frame relay, asynchronous transfer mode ("ATM"), integrated digital services network ("ISDN"), personal communications services ("PCS"), transmission control protocol/Internet protocol ("TCP/IP"), serial line Internet protocol/point to point protocol ("SLIP/PPP"), and so on, but may also implement customized or non-standard interface protocols as well.

Software and data transferred via communication interface 974 are generally in the form of electrical communication signals 978. These signals 978 are preferably provided to communication interface 974 via a communication channel 976. Communication channel 976 carries signals 978 and can be implemented using a variety of communication means including wire or cable, fiber optics, conventional phone line, cellular phone link, radio frequency (RF) link, or infrared link, just to name a few.

Computer executable code (i.e., computer programs or software) is stored in the main memory 996 and/or the secondary memory 958. Computer programs can also be received via communication interface 974 and stored in the main memory 996 and/or the secondary memory 958. Such computer programs, when executed, enable the computer system 950 to perform the various functions of the present invention as previously described.

In this description, the term "computer readable medium" is used to refer to any media used to provide computer executable code (e.g., software and computer programs) to the computer system 950. Examples of these media include main memory 996, secondary memory 958 (including hard disk drive 960, removable storage medium 964, and external storage medium 972), and any peripheral device communicatively coupled with communication interface 974 (including a network information server or other network device). These computer readable mediums are means for providing executable code, programming instructions, and software to the computer system 950.

In an embodiment that is implemented using software, the software may be stored on a computer readable medium and loaded into computer system 950 by way of removable storage drive 962, interface 970, or communication interface 974. In such an embodiment, the software is loaded into the computer system 950 in the form of electrical communication signals 978. The software, when executed by the processor 952, preferably causes the processor 952 to perform the inventive features and functions previously described herein.

Various embodiments may also be implemented primarily in hardware using, for example, components such as application specific integrated circuits ("ASICs"), or field programmable gate arrays ("FPGAs"). Implementation of a hardware state machine capable of performing the functions described herein will also be apparent to those skilled in the relevant art. Various embodiments may also be implemented using a combination of both hardware and software.

While the particular systems and methods herein shown and described in detail is fully capable of attaining the above described objects of this invention, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly limited by nothing other than the appended claims.

What is claimed is:

1. A computer implemented method for viewing on a virtual microscope slide client viewer virtual microscope slides stored in a persistent data storage area on a virtual microscope slide image server, wherein a stored virtual microscope slide image includes image data at a plurality of resolutions, the method comprising:

receiving at the virtual microscope slide image server a virtual microscope slide request from the virtual microscope slide client viewer, wherein the request identifies a stored virtual microscope slide having a plurality of images of the entire virtual slide, wherein each of said plurality of images of the entire virtual slide is at a different resolution, said request further identifying a particular resolution for the requested virtual microscope slide image data;

determining the requested resolution, wherein the requested resolution is not one of the plurality of resolutions in the stored virtual microscope slide;

obtaining virtual microscope slide image data from the stored virtual microscope slide image, wherein the obtained image data is from the resolution of the plurality of stored resolutions that is nearest to the requested resolution;

sending the obtained virtual slide image data to the virtual microscope slide client viewer; and scaling the virtual slide image data at the client viewer from the stored resolution to the requested resolution.

2. A computer implemented method for viewing on a client viewer image data stored in a persistent data storage area on an image server, wherein a stored image includes image data at a plurality of resolutions and annotation data that is associated with a particular location relative to the base resolution of the image, the method comprising:

receiving at the image server an image request from the client viewer, wherein the request identifies a particular region of a stored image and a particular resolution for the requested image, wherein the requested resolution is not the base resolution;

determining that the requested region at the base resolution of the stored image has associated annotation data;

determining coordinates for said associated annotation data, said coordinates relative to said base resolution of the stored image;

scaling the associated annotation data from the base resolution to the requested resolution in accordance with said coordinates;

providing the requested image data and scaled associated annotation data on a display of the client viewer, wherein the scaled associated annotation data is presented on the display as an overlay of the requested image data at said coordinates.

3. The method of claim 2 wherein the annotation data comprises one or more annotation layers to be overlaid over the stored image.

4. The method of claim 3 wherein each annotation layer includes one or more displayed features or regions selected by a user.

5. The method of claim 3 wherein each annotation included in an annotation layer is displayed in a different color.

6. The method of claim 3 wherein each annotation layer can be selectively enabled or disabled.

7. The method of claim 2 wherein the annotation data is stored as a string of a structured language.

8. The method of claim 7 wherein the annotation data is stored as a string of data written in a structured language.

9. The method of claim 8 wherein the annotation data is stored as an extensible markup language ("XML") string.

10. The computer implemented method of claim 1
    wherein the virtual microscope slide request identifies a particular region of the stored virtual microscope slide image;
    wherein obtaining virtual microscope slide image data further comprises obtaining one or more data blocks from the stored virtual microscope slide image, wherein the obtained one or more data blocks correspond to the requested region and include more image data than the requested region; and
    further comprising constructing the requested region from the one or more data blocks at the client viewer.

11. The computer implemented method of claim 1 wherein the virtual slide image includes a checksum to validate image integrity of the virtual slide image, the checksum being calculated at a block level.

12. The computer implemented method of claim 1 wherein the plurality of images of the entire virtual slide are organized as a sequence of blocks.

13. The computer implemented method of claim 12 wherein the blocks are compressed individually.

14. The computer implemented method of claim 1 further comprising storing the scaled image at the virtual microscope slide image server in association with the requested virtual microscope slide.

15. The computer implemented method of claim 14 wherein storing the scaled image further comprises storing the scaled image in a viewer cache.

16. The computer implemented method of claim 14 wherein storing the scaled image further comprises storing the scaled image in a server cache.

* * * * *